(12) United States Patent
Behlke et al.

(10) Patent No.: US 7,112,406 B2
(45) Date of Patent: Sep. 26, 2006

(54) POLYNOMIAL AMPLIFICATION OF NUCLEIC ACIDS

(75) Inventors: Mark Aaron Behlke, Coralville, IA (US); Joseph Alan Walder, Chicago, IL (US); Jeffrey A. Manthey, Iowa City, IA (US)

(73) Assignee: Integrated DNA Technologies, Inc., Coralville, IA (US)

( * ) Notice: Subject to any disclaimer, the term of this patent is extended or adjusted under 35 U.S.C. 154(b) by 378 days.

(21) Appl. No.: 10/377,168

(22) Filed: Feb. 28, 2003

(65) Prior Publication Data

US 2004/0248095 A1    Dec. 9, 2004

Related U.S. Application Data

(60) Provisional application No. 60/360,995, filed on Mar. 1, 2002.

(51) Int. Cl.
*C12Q 1/68*   (2006.01)
*C12P 19/34*   (2006.01)

(52) U.S. Cl. .................... 435/6; 435/91.1; 435/91.2
(58) Field of Classification Search ...................... None
See application file for complete search history.

(56) References Cited

U.S. PATENT DOCUMENTS

| | | | |
|---|---|---|---|
| 4,683,195 A | | 7/1987 | Mullis et al. |
| 5,422,252 A | | 6/1995 | Walker et al. |
| 5,455,166 A | | 10/1995 | Walker |
| 5,641,864 A | * | 6/1997 | Gelfand ..................... 530/350 |
| 5,683,896 A | | 11/1997 | Hartley et al. |
| 5,824,517 A | | 10/1998 | Cleuziat et al. |
| 6,027,923 A | | 2/2000 | Wallace |
| 6,124,120 A | | 9/2000 | Lizardi |
| 6,143,495 A | * | 11/2000 | Lizardi et al. ................. 435/6 |
| 6,214,587 B1 | | 4/2001 | Dattagupta et al. |
| 6,251,639 B1 | | 6/2001 | Kurn |
| 6,335,184 B1 | | 1/2002 | Reyes et al. |

FOREIGN PATENT DOCUMENTS

EP    0 416817 B1    10/1996

OTHER PUBLICATIONS

Stump et al. Nucleic Acids Res. (1999) 27:4642-4648.*
Loakes et al. Nucleic Acids Res. (1995) 23:2361-2366.*
Garcia-Quintanilla et al., Single- Tube Balanced Heminested PCR for Detecting Mycobacterium Tuberculosis in Smear-Negative Samples, *Journal of Clinical Microbiology*, vol. 38, No. 3, 2000, 1166-1169.
Little et al., Strand Displacement Amplification and Homogenous real-Time Detection Incorporated in a Second-Generation DNA Probe System, BDProbeTecET, *Clinical Chemistry*, 45:6, 1999, 777-784.
Nycz et al., Quantitative Reverse Transcription Strand Displacement Amplification: Quantitation of Nucleic Acids Using an Isothermal Amplification Technique, *Analytical Biochemistry*, 259, 1998, 226-234.

(Continued)

*Primary Examiner*—Jeffrey Fredman
*Assistant Examiner*—David C. Thomas
(74) *Attorney, Agent, or Firm*—Darby & Darby

(57) ABSTRACT

The invention provides methods and compositions for the amplification and replication of nucleic acid molecules. In particular, novel amplification methods, referred to herein as polynomial amplification, are provided. According to these methods, a nucleic acid molecule to be amplified is contacted with at least two primers; a non-replicable primer which may hybridize to the nucleic acid molecule being amplified, and a replicable primer which may hybridize to a primer extension product generated from extension of the non-replicable primer.

5 Claims, 10 Drawing Sheets

OTHER PUBLICATIONS

Lizardi et al., Mutation Detection and Single-Molecule Counting using Isothermal Rolling-Circle Amplification, *Nature Genetics*, vol. 19, 1998, 225-232.

Poddar, Symmetric vs Asymmetric PCR and Molecular Beacon Probe in the Detection of a Target Gene of Adenovirus, *Molecular and Cellular Probes*, 14, 2000, 25-32.

Eritja et al., Synthesis of Oligonucleotides Containing the Abasic Site Model Compound 1,4-Anhydro-2-Deoxy-D-Ribitol, Nucleosides & Nucleotides, vol. 6. No. 4, 803-814; 1987.

Kwok and Higuchi, Avoiding false positives with PCR, Nature, vol. 339, May 1989, 237-238.

Saiki et al., Enzymatic Amplification of B-Globin Genomic Sequences and Restriction Site Analysis for Diagnosis of Sickle Cell Anemia, Science vol. 230, 1350-1354; 1985.

Newton et al., Analysis of any point mutation in DNA. The amplification refractory mutation system (ARMS), Nucleic Acid Research, vol. 17, No. 7, 1989, 2504-2516.

Seela et al., Oligodeoxyribonucleotides containing 1,3-propanediol as nucleoside substiture, Nucleic Acids Research, vol. 15, No. 7, 1987, 3113-3129.

Longo et al., Use of uracil DNA glycosylase to control carry-over contamination in polymerase chain reactions, Gene, 93(1); 1990, 125-128.

Ugozzoli and Wallace, Allele-Specific Polymerase Chain Reaction, Methods, vol. 2, No. 1, Feb. 1991, 42-48.

Reyes et al., Linked Linear Amplification: A New Method for the Amplification of DNA, Clinical Chemistry 2001, 47:1, 31-40.

Wu and Wallace, The Ligation Amplification Reaction (LAR)- Amplification of Specific DNA Sequences Using Sequential Rounds of Template-Dependent Ligation, Genomics, vol. 4, 1989, 560-569.

Newton et al., The Production fo PCR products with 5' single-stranded tails using primers that incorporate novel phosphoramidite intermediates, Nucleic Acids Research, vol. 21, No. 5, 1993, 1155-1162.

Gade et al., Incorporation of Nonbase Residues into Synthetic Oligonucleotides and Their Use in the PCR, Gata 10(2), 1993, 61-65.

Walder et al., use of PCR primers containing a 3'-terminal ribose residue to prevent cross-contamination of amplified sequences, Nucleic Acids Research vol. 21, No. 18, 1993, 4339-4343.

Walker et al., Strand displacement amplification—an isothermal, in vitro DNA amplification technique, Nucleic Acids Research, vol. 20, No. 7, 1992, 1691-1966.

* cited by examiner

A) Polymerase Chain Reaction (PCR)

2-Primer     Hemi-nested     Nested

B) Linear Amplification        Linked Linear Amplification (LLA)

1 or 2-Primer        Nested

C) Polynomial Amplification

2-Primer        Hemi-nested

| Cycle # | Reaction Events | Species |
|---|---|---|
| Start | For-1 ~~~~~~~~~~~~~~~~~~~ Rev | A<br>B |
| 1 | ~~~~~~~~~~~~~~~~~~~ ←————————<br>————————→ ~~~~~~~~~~~~~~~~~~~ | A<br>D, made from A<br>C, made from B<br>B |
| 2 | ————————————<br>←——————————<br>——————————→<br>————————————— | E, made from D<br>D<br>C<br>F, made from C |
| 3 | ———————————<br>——————————— | E<br>F, made from E |

Figure 2

Rat CP Gene Target

```
        For-1                        For-2
TAATACGACTCACTATAGACATGGTCAACCCCACCGTGTTCTTCGACATCACGGCTG

For-3                Probe                    Rev-3
ATGGCGAGCCCTTGGGTCGCGTCTGCTTCGAGCTGTTTGCAGACAAAGTTCCAAAGA Rev-2
CAGCAGAAAACTTTCGTGCTCTGAGCACTGGGGAGAAAGGATTTGGCTATAAGATGA Rev-1
TACACTCCGACATAACGTGGATCC
```

SEQ ID No. 11

POLYNOMIAL AMPLIFICATION OF NUCLEIC ACIDS

This patent application claims the priority of U.S. provisional patent application No. 60/360,995, filed Mar. 1, 2002, which is incorporated herein by reference.

FIELD OF THE INVENTION

The present invention relates to the field of nucleic acid replication and amplification. More specifically, the invention relates to methods and processes for amplifying nucleic acid sequences in vitro. The invention also relates to various applications for which such nucleic acid amplification methods may be used, including the detection of nucleic acid sequences, e.g., for the diagnosis of diseases and disorders, the genotyping of individuals, nucleic acid sequencing and forensics applications to name a few.

BACKGROUND OF THE INVENTION

The extensive replication of nucleic acids, today known as (and referred to herein as) nucleic acid "amplification," finds wide utility, both practical and theoretical, in a variety of contexts. H. G. Khorana and his co-workers first proposed the use of an in vitro DNA amplification process to increase available amounts of double-stranded DNA (partial sequences of the gene for the major yeast alanine t-RNA) that had been created by the enzymatic ligation of synthetic DNA's. See K. Kleppe et al., *J. Mol. Biol.* 56:341–361 (1971). Later, in vitro amplification was applied to the amplification of genomic DNA (Saiki et al., *Science* 230: 1350–1354 (1985)) as the technique now known as the polymerase chain reaction or "PCR." Through the wide availability of synthetic oligonucleotide primers, thermostable DNA polymerases and automated temperature cycling apparatus, PCR became a widely utilized tool of the molecular biologist.

The PCR process is also referred to in the literature as an "exponential amplification" process. Each round or "cycle" of primer extension results in replication of a primer-binding site for the other primer. Thus, each of the synthetic DNA molecules produced in any of the previous cycles is available to serve as a template for primer-dependent replication. This aspect of the process, coupled with the presence of a sufficiently large number of primer molecules, results in synthetic DNA accumulating in a mathematically exponential manner as the reaction proceeds.

PCR has proven to be a valuable technique for the molecular biologist, and has been used extensively in the fields of human genetic research, diagnostics and forensic science, and even in the detection of antibodies. However, disadvantages have nevertheless been recognized. The PCR process can be difficult to quantify accurately, mainly because the amplification products increase exponentially with each round of amplification. The products of PCR, namely, double-stranded DNA molecules, are difficult to analyze or sequence per se. Strand separation typically must be carried out prior to sequencing or other downstream processes that requires single stranded nucleic acids, such as hybridization to a probe capable of detecting the sequence of interest.

The PCR process also has proven to be quite susceptible to contamination generated through the transfer of previously amplified DNA sequences into a new reaction. Such contamination is referred to as carry-over contamination and can cause false-positive results. Carry-over contamination appears to be caused by the facts that (1) very large amounts of DNA are generated in any given reaction cycle, and (2) the process uses all product DNA strands as templates in subsequent cycles. Even minute quantities of contaminating DNA can be exponentially amplified and lead to erroneous results. See Kwok and Higuchi, Nature 339:237–238 (1989). False positive results in a clinical setting can lead to incorrect therapeutic interventions. While useful in any setting, amplification methods that reduce risk of carry-over contamination will have particular utility in clinical diagnostic assays.

As these contamination problems are widely recognized, several approaches have been designed to help limit the risk of product contamination in PCR, including chemical decontamination, utilizing closed systems, use of ultraviolet irradiated work stations (Pao et al, *Mol. Cell Probes* 7: 217–9 (1993)), cleavable primers (Walder et al., *Nucleic Acids Research* 21:4, 229–43 (1993)), or enzymatic degradation methods (Longo et al., *Gene* 93: 125–8 (1990)). None of these methods is totally effective.

A technique that significantly reduces this risk of carry-over contamination has been developed. This technique, linked linear amplification (herein also referred to as "LLA"), uses primers that are modified in such a way that they are, or are rendered, replication defective. Primers that have a blocking group, such as 1,3 propanediol, can support primer extension but cannot be replicated. Therefore, primer extension reactions are terminated when they reach the blocking group, or non-replicable element, of a primer that has been incorporated into a template strand. See, for example, U.S. Pat. Nos. 6,335,184 and 6,027,923. See, also, Reyes et al. *Clinical Chemistry* 47:1 31–40 (2001); Wu et al. *Genomics* 4: 560–569 (1989).

Because the primer extension products in LLA cannot serve as a template for subsequent primer binding and primer extension, LLA molecules accumulate in a mathematically linear fashion. The linear accumulation of LLA products renders this process relatively insensitive to carry-over contamination. Although decreased risk of contamination is an advantage of the LLA system, the linear accumulation of LLA products also results in a great disadvantage of this system: LLA requires that an excessive number of reaction cycles and/or primers be used in order to achieve significant amplification. For example, U.S. Pat. No. 6,335, 184 discloses that 1,000 cycles would be necessary in order to generate a yield of 500,500 products. Furthermore, Reyes et al., *Clinical Chemistry* 47:31–40 (2001) discloses that 14 to 18 primers were necessary in order to achieve yields comparable with PCR.

Designing and synthesizing such a large number of primers is time consuming, expensive and difficult. In many cases it may not be possible to obtain the number of functional primers needed for LLA; there simply may not be a sufficient number of acceptable primer-binding sites available.

Obtaining single-stranded product from nucleic acid amplification is particularly useful since many applications for which nucleic acid amplification is employed require a single-stranded nucleic acid. For example, single-stranded nucleic acid amplification products are immediately available for detection by hybridization with a labeled probe. This is particularly useful for diagnostic tests. A single-stranded nucleic acid amplification product can also be immediately sequenced or used as a probe itself. In amplification systems where both strands are equally amplified, such as in traditional PCR and LLA reactions, reannealing of the complementary strands can compete with binding of the labeled probe and interfere with detection of the target, sequencing, probing, etc. Both LLA and PCR require a minimum of 3 primers to yield a single-stranded product and if increased amplification power is desired, more primers may be required to yield a single-stranded product.

Therefore, there is a need for robust nucleic acid amplification systems that produce single-stranded nucleic acid products and pose minimal levels of carry-over contamination.

SUMMARY OF THE INVENTION

The present invention solves many of the above-described problems in the art by providing novel, improved methods for amplifying nucleic acid molecules. In particular, Applicants have discovered that a nucleic acid molecule of interest (e.g., in a sample) may be amplified by using a combination of at least two nucleic acid primers. At least one of the primers used in these novel amplification methods is preferably a non-replicable primer and may be modified (e.g. with a blocking group) in such a way that it is or may be rendered replication defective. In contrast, however, to existing nucleic acid amplification methods that use non-replicable primers, the nucleic acid amplification methods of the present invention may also use a second primer that is not replication defective (i.e., a "replicable" primer). Surprisingly, these nucleic acid amplification methods of the invention are able to substantially reduce or even eliminate carry-over contamination, e.g., from the amplification of undesired or contaminating sequences. However, unlike existing methods that use blocked or non-replicable primers, the methods of this invention are able to produce nucleic acid amplification products that increase in a mathematically polynomial fashion. Thus, the methods of the present invention are able to produce relatively large amounts of amplified nucleic acid in fewer amplification cycles and from smaller amounts of sample than existing methods, such as LLA.

Accordingly, the invention provides novel methods for amplifying a nucleotide sequence of interest from a nucleic acid. These methods comprise, in preferred embodiments, a step of contacting a nucleic acid molecule to be amplified with a primer set, which comprises (i) a non-replicable primer that hybridizes to the nucleic acid molecule, and (ii) a replicable primer that hybridizes to a primer extension product that is generated by replication of the nucleic acid from the non-replicable primer. The non-replicable and replicable primers are preferably contacted to the nucleic acid molecule under conditions so that a first generation primer extension product, capable of hybridizing to the replicable primer, is produced by using the nucleic acid molecule to be amplified as a template and the non-replicable primer as a primer. The methods of the invention may also involve steps of separating the first generation primer extension products from the respective templates, thereby producing single-stranded molecules, and treating the first generation primer extension products with the aforementioned non-replicable and replicable primers so that second generation primer extension products are produced by using the first generation primer extension products as templates for the replicable primer and the nucleic acid as a template for the non-replicable primer. These steps may then be repeated for as many times as desired to amplify the nucleic acid sequence to an extent desired, e.g., by a user.

In various embodiments of the invention, the non-replicable primer may comprise, e.g., a tandem pair of base analogs or internucleotide extenders, or even a combination thereof. For example, in various embodiments of the invention the non-replicable primer may comprise a non-replicable element, which may be selected from the group consisting of 5-nitroindole; 1,3-propanediol; and an abasic ribose group to name a few. Other exemplary non-replicable elements which may be used are described, infra. In still other embodiments, a non-replicable primer of the invention may comprise a cleavable element.

In other embodiments, the primer set(s) used in the methods of this invention may comprise a nested non-replicable primer which hybridizes to the nucleic acid and to the second generation extension product. In still other embodiments, the primer set(s) used in these methods may comprise a plurality of nested non-replicable primers. For example, a primer set used in the methods of this invention may comprise a second non-replicable primer which hybridizes to (i) the nucleic acid, (ii) to the second generation extension product; and (iii) to a primer extension product generated by replication from the replicable primer and extension products of the nested non-replicable primer.

The invention also provides methods for preparing primers which may be used in accordance with the amplification methods of this invention. Such methods generally comprise steps of (a) designing a primer set, and (b) synthesizing the primers in the primer set. In preferred embodiments, the primer set designed will comprise at least (i) a set of nested, non-replicable primers that are each capable of hybridizing to a same single stranded nucleic acid, and (ii) a replicable primer that is capable of hybridizing to a primer extension product generated by replication of the single stranded nucleic acid and the non-replicable primers. The number of non-replicable primers in the primer set designed by such a method will preferably be determined by calculating a number of non-replicable primers needed for a number of synthetic cycles to obtain a desired amount of amplified nucleotide sequence.

In other embodiments, the invention also provides kits comprising one or more primer sets. In particular, the primer sets contained in such kits are ones designed according to the above-described methods of the invention and/or which are suitable for use in the amplification methods of the invention, described supra.

Still other embodiments are described throughout the application which a skilled artisan will recognize as part of the present invention.

DESCRIPTION OF THE DRAWINGS

FIG. 2. Two-primer polynomial amplification is shown schematically. Starting target nucleic acids are represented by wavy lines. The forward primer is indicated by a right directed triangle and includes modifying group(s) to block DNA synthesis template function as indicated. The reverse primer is indicated by a left directed triangle. Reaction products are represented by straight lines. Reaction species are labeled using standard nomenclature as described in text. Only new reaction events are shown as they occur in each specified cycle; as in any cycling reaction, "old events" continue to occur in subsequent cycles and accumulate.

FIG. 7. Experimental design to test polynomial amplification method on a cloned target nucleic acid. The sequence of the target nucleic acid is shown (SEQ. ID NO. 11). The position of forward primers (For-1, For-2, For-3), reverse primers (Rev-1, Rev-2, Rev-3), and probe for oligonucleotide hybridization sites within the target are underscored.

DETAILED DESCRIPTION

Figure 1:
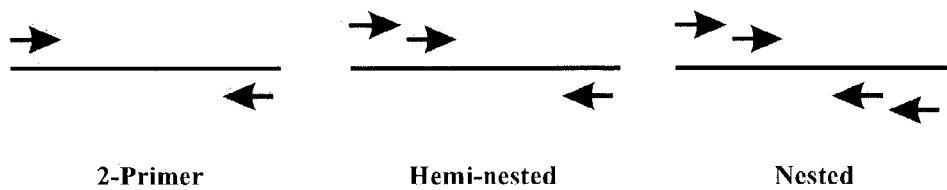
FIGS. 1A, 1B, and 1C. Schematic of nucleic acid amplification methods. A. Variants of a polymerase chain reaction (PCR) method already known in the art shown, including conventional 2 primer PCR, 3 primer hemi-nested PCR, and 4 primer nested PCR. B. Linear amplification methods already known in the art utilizing blocked primers are shown, including direct 2 primer and nested multi-primer variants. C. Polynomial amplification of the invention is shown, including 2 primer and hemi-nested multi-primer methods.
Figure 1:
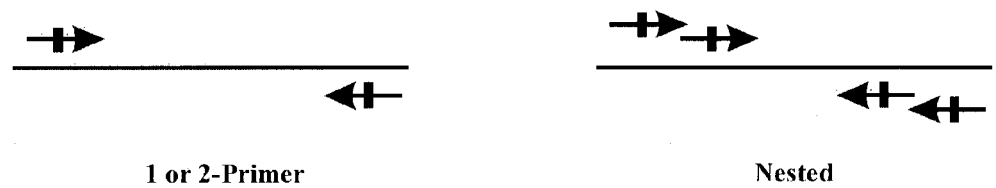
Figure 1:
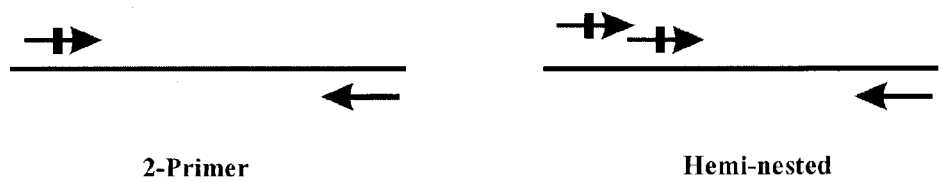

As noted above, the present invention provides for amplifying a nucleotide sequence of interest from a nucleic acid. More importantly, the invention provides for amplifying a nucleic acid sequence to produce a predominantly "sterile" nucleic acid product with a very high degree of amplification. Such nucleic acid products are described in more detail, infra. The production of predominantly sterile extension products and the amplification achieved by this invention are evident from the polynomial amplification, explained in greater detail below, that is achieved.

In particular, a nucleic acid molecule of interest may be amplified in accordance with the present invention by using a set of at least two primers, at least one of which is modified (e.g., with a blocking group) in such a way that it is or may be rendered replication defective. However, unlike existing methods that use such "non-replicable" primers (for example, the LLA methods described, supra) the nucleic acid amplification methods of this invention also use a second primer, which is unmodified or "replicable." Applicants have discovered that, by using such a combination of replicable and non-replicable primers, the amount of carry-over contamination is greatly reduced or even eliminated. At the same time, such methods are able to produce relatively large amounts of amplified nucleic acid in fewer amplification cycles and from a smaller amount of sample than existing amplification methods, such as LLA.

The term nucleic acid generally refers to a single stranded or double stranded polymer of nucleotide bases, either deoxyribonucleic acid (DNA) bases or ribonucleic acid (RNA) bases. In the context of the present invention, the nucleic acid containing a sequence of interest can be from any source, including genomic DNA, cDNA, a complementary strand of either, mRNA, etc. When the nucleic acid of interest is RNA, preferably the RNA is reverse transcribed to DNA prior to amplifying it in accordance with the invention. The nucleic acid products of these replication reactions, typically DNA because the synthesis is more straightforward, are referred to herein as a "primer extension products" because formation of the nucleic acid product depends on primer hybridization to the template nucleic acid strand and extension or polymerization from the 3' end of the primer.

A "first generation" primer extension product is used herein to refer to a product produced from hybridization of a primer with the nucleic acid containing the nucleotide sequence of interest. More particularly, it refers to a product produced from hybridization of a non-replicable primer with such nucleic acid. Similarly, a "second generation" primer extension product is produced by priming and replication of the first generation extension product by the replicable primer. One can envision higher order of magnitude primer extension products from nested primers. Furthermore, the designation of "first generation" and "second generation" for purposes of description does not imply that other primer extension products from an initial or subsequent synthetic cycle may not be formed as described below.

A primer is a relatively short (further described infra) nucleic acid (also referred to as an "oligonucleotide") that is capable of hybridizing to a larger nucleic acid; e.g., the nucleic acid containing a nucleotide sequence of interest or a primer extension product nucleic acid. As discussed in greater detail below, depending on their function (non-replicable versus replicable, for example), the oligonucleotide primers may contain DNA or RNA. Primers used in the present invention may also contain RNA bases in a predominantly DNA sequence, base analogs in a predominantly DNA sequence, etc.

The term "template" merely refers to a single stranded nucleic acid that is replicated after primer hybridization by a nucleic acid polymerase, e.g., DNA polymerase, yielding a double stranded nucleic acid consisting of the template and the new "daughter" strand. The term "replication" has its ordinary meaning, i.e., synthesis of a complementary nucleic acid strand. In order to replicate a nucleic acid template, the template must be at least partially single stranded. Separation of double stranded nucleic acids to form single stranded templates can occur by a number of mechanisms, as discussed in greater detail infra, including by heat denaturing (e.g., by thermal cycling), strand displacement, and the like. In the context of the present invention, each such strand separation followed by primer annealing and extension constitutes a "cycle".

"Amplification" as used herein refers to the total number of primer extension product nucleic acid molecules produced from each nucleic acid containing the nucleotide sequence of interest. The term amplification is also used to describe the use of reactions to increase the concentration of a particular sequence within a mixture of nucleic acid sequences. It can specifically refer to the predominant species of primer extension product, which, as discussed below, can constitute upwards of 80% of the total of primer extension products. The amount of amplification in accordance with this invention can be determined or estimated by a polynomial equation which, after about ten or more synthetic cycles, simplifies to the equation:

$$\frac{n^x}{x!},$$

in which n is the number of cycles, x is equal to 2y−1, and y is the total number of primers (nested non-replicable primers plus replicable primer) in the primer set.

As used herein, the term "polynomial amplification" (herein referred to also as "PA") refers generally to methods and systems of this invention, including kits and amplification reaction mixtures. More specifically, the term PA refers to the amplification methods described above, i.e., using a non-replicable primer or nested set of primers to replicate one strand of a nucleic acid, and a replicable primer to initiate replication of the complementary strand (if present) and/or of the first generation primer extension product of a non-replicable primer. This highly effective and powerful system limits the number of amplification cycles required and priming reagents required to achieve the desired level of amplification for detection of product. How the power of the present invention achieves these dual advantages will be more apparent from the detailed description that follows.

As one of skill can appreciate, equations to calculate the amount or degree of amplification represent hypothetical amplification under ideal conditions. The actual degree of amplification may approach but generally will not actually equal the calculated amount. Nevertheless, such equations provide useful representations for the amplification methods of this invention, and the actual level of amplification may well be approximated or estimated with such equations.

Various factors may affect the fit of experimental versus expected amplification, such as efficiency of priming, efficiency of replication, read-through of the blocked primer, and other factors that can be measured and accounted for. However, even to the degree that the polynomial equations elaborated herein are approximations, they demonstrate the high degree of amplification the invention achieves.

A nucleotide sequence is a specific arrangement of bases in a nucleic acid. Every nucleic acid has a particular nucleotide sequence. The nucleotide sequence of a nucleic acid determines its identity, and also affects selection of primer sequences (for hybridization at the desired melting temperature, $T_m$) and probe sequences. The present invention provides methods for amplifying, and thus, in many cases, detecting the presence of a nucleotide sequence in a nucleic acid; the products of the invention are themselves nucleic acids which in turn contain all or a substantial part of the nucleotide sequence of interest, or its complement.

The term "sterile" is used to characterize the amplification products of the invention. In particular, the predominant number of such products will not serve as templates for further amplification reactions, and therefore will not act as a contaminant. As shown quantitatively below, by far the predominant species of molecule present in a reaction of the invention will be a nucleic acid that is incapable of hybridization with any primers used in the amplification system. For example, depending on the number of cycles of replication, operation of the invention in its simplest form will result in a product in which 80% or more of the primer extension products will be fully incapable of serving as a template for further replication. After additional replication cycles, the relative amount of contaminating nucleic acids is substantially reduced, to the point where their levels become insignificant or even undetectable.

To reiterate, the invention involves contacting a nucleic acid containing the nucleotide sequence of interest with a primer set. Primer sets of the invention preferably comprise at least two components: a non-replicable primer or a set of nested non-replicable primers that hybridize to the nucleic acid containing the nucleotide sequence of interest; and a replicable primer that is capable of hybridizing to a primary extension product generated by replication of the nucleic acid from any of the non-replicable primer or primers. For example, if the nucleic acid is a double-stranded nucleic acid, the replicable primer may be capable of hybridizing to a nucleic acid that is itself complementary to the strand to which the non-replicable primer or primers are capable of hybridizing.

Replication from the non-replicable primer preferably yields a primer extension product able to serve as a template for primer-initiated replication from the replicable primer. However, this template will cause replication to halt before complete synthesis of the complementary sequence of the non-replicable primer. Thus, the primer extension product generated from the replicable primer cannot serve as a template for replication with the non-replicable primer.

The term "non-replicable primer" refers to a primer that contains non-replicable elements. Such elements may include, but are by no means limited to, a non-replicable base analog(s), internucleotide extender(s), or a cleavable element(s) positioned so as to block or prevent synthesis of a complementary strand that would support primer extension. A base analog and an internucleotide extender are herein referred to as chemical groups that can substitute for a nucleotide base but which cannot be replicated. The presence of a base analog or internucleotide extender in a primer blocks DNA polymerase from replicating such a primer. Alternatively, modification of a primer to contain a cleavage site ("cleavable element"), preferably a cleavage site that is readily cleaved with or shortly after replication, may also provide a non-replicable primer. As those skilled in the art can readily appropriate, cleaving the primer sequence in a primer extension product provides a truncated product whose complementary strand is incapable of hybridizing to the non-replicable primer. Specific sections, infra, explore, in detail, the nature and chemistry of non-replicable primers, non-replicable elements, and cleavable elements.

As used herein, the term "block" is used functionally and does not require absolute blockage. Preferably, the non-replicable element inhibits primer extension in cycling conditions by at least about 90%, more preferably at least about 99%, and most preferably at least about 99.9%. More preferably, the term "block" means that there is only a low level, if any, of detectable read-through products. As with all biological processes, the ability to inhibit the activity of DNA polymerase will depend on a number of factors. For example, in some embodiments achieving absolute inhibition of replication might result in inactivating the ability of the primer to hybridize, abolishing its purpose altogether. A skilled artisan will appreciate that a certain tradeoff of hybridization ability and replication blocking ability maybe necessary in practicing the PA methods of this invention. As discussed in greater detail below, certain base analogs can be employed that are very effective in blocking replication, and either do not adversely impact or actually increase $T_m$'s of hybridization of all the nucleotide primers containing them. Thus, one of the advantages of the invention is the ability to overcome certain of the tradeoffs believed to be necessary in prior art technologies that also employed non-replicable primers.

The term "replicable primer" refers to a primer that is fully capable of acting as a template for DNA polymerase in supporting replication to the end of the primer sequence. Thus, a replicable primer may be functionally identical to the primers used in traditional PCR reactions.

The term "nested," when used to describe primers, has its ordinary meaning in the art of nucleic acid hybridization. Specifically, "nested primers" are capable of hybridizing to positions on the nucleic acid adjacent to the nucleotide sequence of interest that are bracketed by the most distal primer pair positions (i.e., the non-replicable primer and position of hybridization of the replicable primer on the complementary nucleic acid strand that are farthest apart). The term "hemi-nested" means asymmetric nesting, i.e., all the nested primers are capable of binding to the same strand of a nucleic acid template. For purposes of description, the "level" of a nested non-replicable primer refers to its relative proximity to the replicable primer hybridization position. "Level one" (or, alternatively, the first level) is most distal; "level two" refers to the next set of nested primers one "level" closer to the replicable primer, and so forth. Thus, the highest "level" of nesting primers corresponds to the closest in proximity of any primer pair. A "primer pair" is a non-replicable primer and the replicable primer, either one of which can be regarded as a "forward" primer with the other being the "reverse" primer. Generally, the term "forward" will be used herein to refer to a non-replicable primer. Thus, a "forward-1" (or "For-1") primer is a level one non-replicable primer; and For-3 is a level three non-replicable primer; and Rev (reverse) is the replicable primer.

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); Oligonucleotide Synthesis (M. J. Gait Ed. 1984); Nucleic Acid Hybridization (B. D. Hames & S. J. Higgins eds. (1985)); Transcription And Translation (B. D. Hames & S. J. Higgins, Eds. (1984)); Animal Cell Culture (R. I. Freshney, ed. (1986)); Immobilized Cells And Enzymes (IRL Press, (1986)); B. Perbal, A Practical Guide To Molecular Cloning (1984); F. M. Ausubel et al. (eds.), Current Protocols in Molecular Biology, John Wiley & Sons, Inc. (1994).

As used herein the term "about" or "approximately" means within an acceptable error range for the value being measured. For example, it can mean within 20%, preferably within 10%, and more preferably within 5% of a given value or range. Alternatively, where quantities are specified or approximated by an order of magnitude (e.g., about 10, about $10^3$, about $10^{-2}$, etc.), the term "about" can mean within an order of magnitude of a given value, and preferably within one-half an order of magnitude of the value.

A Comparison of PCR, LLA, and PA

FIGS. 1A, 1B, and 1C present schematic representations of three nucleic acid amplification methods. FIG. 1A illustrates 3 variants of traditional PCR: 2 primer PCR, 3 primer hemi-nested PCR, and 4 primer nested PCR. None of the primers has a non-replicable element in such traditional PCR. FIG. 1B illustrates a linear amplification reaction (LA) involving one or two primers, each of which has a non-replicable element. FIG. 1B also illustrates nested linked linear amplification (LLA), which involves a symmetric distribution of nested primers, each of which has a non-replicable element. FIG. 1C illustrates 2-primer and hemi-nested polynomial amplification. Both 2-primer and hemi-nested polynomial amplification are disclosed in detail in the description and Examples below.

Figure 3:
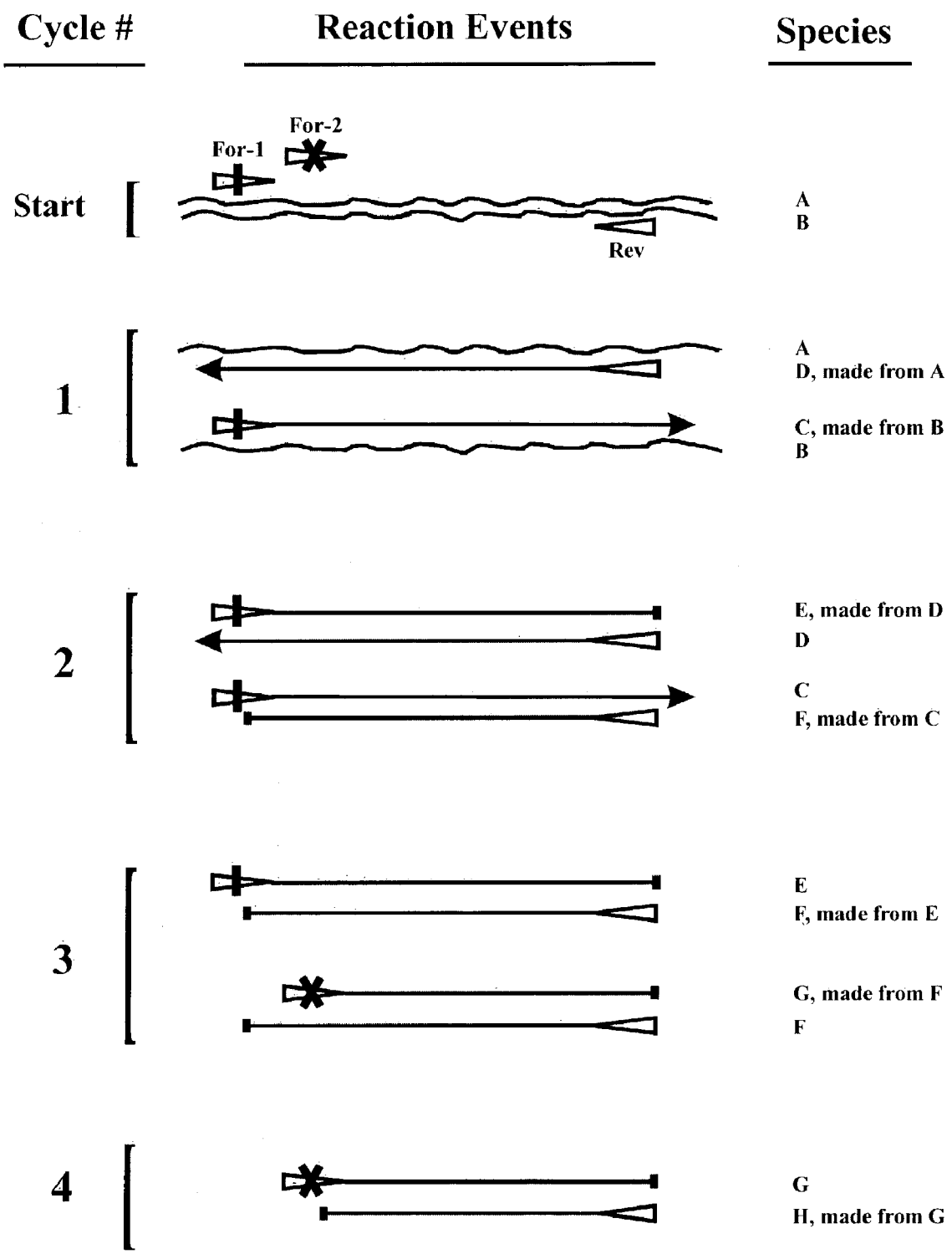
FIG. 3. Three primer nested polynomial amplification is shown schematically. Starting target nucleic acids are represented by wavy lines. Forward primers are indicated by right directed triangles and include modifying group(s) to block DNA synthesis template function as indicated. The reverse primer is indicated by a left directed triangle. Reaction products are represented by straight lines. Reaction species are labeled using standard nomenclature as described in text. Only new reaction events are shown as they occur in each specified cycle; as in any cycling reaction, "old events" continue to occur in subsequent cycles and accumulate.

FIG. 2 illustrates the general scheme of an exemplary 2-primer polynomial amplification method of the invention. FIG. 3 illustrates an exemplary 3-primer nested polynomial amplification. In each of these sets of figures the starting nucleic acids are represented by wavy lines. The forward primer(s) is indicated by a right directed triangle and includes non-replicable elements to block DNA synthesis template function as indicated. The reverse primer is indicated by a left directed triangle. The starting duplex is denatured, preferably by heating in a buffer solution, and the resulting single strands are contacted with a pair of primers (step (b)). Each primer preferably is provided in substantial molar excess of the starting template strand and the forward primer(s) contains within its sequence a non-replicable element, here denoted by a vertical line through the primer. Under appropriate conditions, the primers anneal to their respective templates and are elongated according to the primer extension reaction in the presence of a DNA polymerase and the four deoxyribonucleotides.

Reaction products are represented by straight lines. Reaction species are labeled using standard nomenclature and their template is listed. Only new reaction events are shown as they occur in each specified cycle. As in any cycling reaction, "old events" continue to occur in subsequent cycles and accumulate. The synthesis of species F and species G in FIG. 2 do not progress beyond the non-replicable element in their corresponding template strands. Species F in the 2-primer scheme (FIG. 2) does not participate further in the primer extension reaction because the molecules do not have an effective binding site for the non-replicable primer(s). However, species F in the 3-primer scheme (FIG. 3) does participate in additional primer extension reactions because it has site for hybridization of the nested For-2 primer. Species H in FIG. 3 does not participate further in primer extension reactions because this product does not have an effective binding site for the non-replicable primer(s). In 2-primer polynomial amplification, product F will be the predominant species produced and will remain mostly single-stranded. In 3-primer polynomial amplification, product H will be the predominant species produced and will remain mostly single-stranded.

Figure 4:
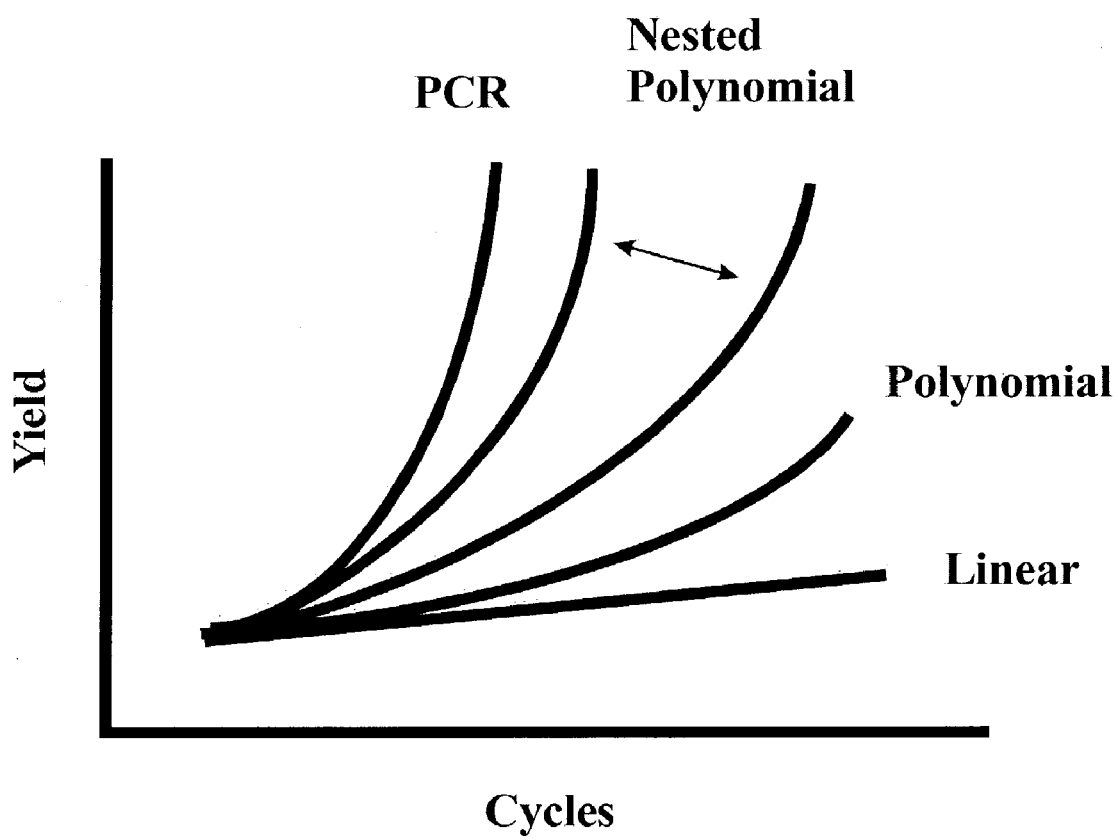
FIG. 4. Graphical representation of relative yield for various amplification methods. Yield for hemi-nested polynomial amplification will vary with number of nested primers employed.

FIG. 4 is a graphical representation comparing the relative mathematical yield from the exemplary methods of linear, Polynomial, nested Polynomial, and PCR described above. The two lines for nested Polynomial illustrate that yield for hemi-nested polynomial amplification increases with the number of nested primers employed.

The amplification power of amplifying a nucleotide sequence of interest using a primer set comprising a non-replicable primer and a replicable primer is shown in Table 1. The accumulation of each amplification species in the amplification reaction can be calculated. For example, Table 1 shows accumulation of the amplification species shown in FIGS. 2 and 3. The equations shown under Table 1 describe the predicted accumulation of amplification species in 2- and 3-primer polynomial amplification, and are polynomial equations. Hence, the amplification of a nucleotide sequence of interest according to these methods is called polynomial amplification.

TABLE 1

Calculated accumulation of Products in 2- and 3-primer polynomial amplification.

| Cycle | Species | | | | | | | | Σ Yield 2-primer | Σ Yield 3-primer |
|---|---|---|---|---|---|---|---|---|---|---|
| | A | B | C | D | E | F | G | H | | |
| Start | 1 | 1 | | | | | | | 2 | 2 |
| 1 | 1 | 1 | 1 | 1 | | | | | 4 | 4 |
| 2 | 1 | 1 | 2 | 2 | 1 | 1 | | | 8 | 8 |
| 3 | 1 | 1 | 3 | 3 | 3 | 4 | 1 | | 15 | 16 |
| 4 | 1 | 1 | 4 | 4 | 6 | 10 | 5 | 1 | 26 | 32 |
| 5 | 1 | 1 | 5 | 5 | 10 | 20 | 15 | 6 | 42 | 63 |
| 6 | 1 | 1 | 6 | 6 | 15 | 35 | 35 | 21 | 64 | 120 |
| 7 | 1 | 1 | 7 | 7 | 21 | 56 | 70 | 56 | 93 | 219 |
| 8 | 1 | 1 | 8 | 8 | 28 | 84 | 126 | 126 | 130 | 382 |
| 9 | 1 | 1 | 9 | 9 | 36 | 120 | 210 | 252 | 176 | 638 |
| 10 | 1 | 1 | 10 | 10 | 45 | 165 | 330 | 462 | 232 | 1024 |
| 20 | 1 | 1 | 20 | 20 | 190 | 1330 | 5985 | 20349 | 1562 | 27896 |
| 30 | 1 | 1 | 30 | 30 | 435 | 4495 | 31465 | 169911 | 4992 | 206368 |
| 40 | 1 | 1 | 40 | 40 | 780 | 10660 | 101270 | 749398 | 11522 | 862190 |
| 50 | 1 | 1 | 50 | 50 | 1225 | 20825 | 249900 | 2349060 | 22152 | 2621112 |

$A = 1$
$B = 1$
$C = n$ (cycle #)
$D = n$
$E = (n^2 - n)/2$
$F = (n^3 - n)/6$
$G = (n^4 - 2n^3 - n^2 + 2n)/24$
$H = (n^5 - 5n^4 + 5n^3 + 5n^2 - 6n)/120$ As more primers are used, the yielded product becomes coincident with the equation in Table 2 (for example, $n^{13}/13!$ for 7 primers, or 5 levels of nesting). At 30 cycles, five levels of nesting result in more product than PCR and at 50 cycles, five levels of nesting result in less product than PCR (Table 2). However, these numbers represent theoretical, not actual, yields. When actual yields are measured, the yields from polynomial amplification can be comparable as shown by the comparison of FIGS. 9a and 9c. For example, one level of nesting (or three primers), results in similar yields of product as PCR (compare FIGS. 9A and 9C).

TABLE 2

Predicted yield in highly nested polynomial amplification.

| Amplification | Nesting | Primers | 30 Cycle Yield | 50 Cycle Yield | Equation (n = cycle #) |
|---|---|---|---|---|---|
| PCR | No | 2 | $1.1 \times 10^9$ | $1.1 \times 10^{15}$ | $2^n$ |
| Polynomial | No | 2 | $4.5 \times 10^3$ | $2.1 \times 10^4$ | $n^3/3!$ |
| | Yes, 1 level | 3 | $2.0 \times 10^5$ | $2.6 \times 10^6$ | $n^5/5!$ |
| | Yes, 2 level | 4 | $4.3 \times 10^6$ | $1.6 \times 10^8$ | $n^7/7!$ |
| | Yes, 3 level | 5 | $5.4 \times 10^7$ | $5.4 \times 10^9$ | $n^9/9!$ |
| | Yes, 4 level | 6 | $4.4 \times 10^8$ | $1.2 \times 10^{11}$ | $n^{11}/11!$ |
| | Yes, 5 level | 7 | $2.6 \times 10^9$ | $2.0 \times 10^{12}$ | $n^{13}/13!$ |

Nucleic Acid Samples

Those skilled in the art will recognize that the nucleic acid to be amplified according to the invention can be from any source. For example, the nucleic acid can come from biopsy samples, cells in culture, transgenic animals, tissue samples, clinical samples, forensic samples, blood samples, etc. The template DNA, for example, can be derived from mRNA by use of reverse transcriptase. While most polymerases prefer to copy DNA templates, reverse transcriptase can be utilized to synthesize DNA copies of RNA templates using procedures well known to those skilled in the art. Other examples of sources for the nucleic acid include genomic DNA, cDNA, and plasmid DNA.

Nucleic acid samples amplified in accordance with the invention may be prepared according to routine techniques of molecular biology that are generally known in the art. See, for example, Ausubel et al., supra, particularly at Chapter 2.

As noted, above, the term nucleic acid generally refers to a single stranded or double stranded polymer of nucleotide bases, such as DNA or RNA. More specifically, the term "nucleic acid" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA—DNA, DNA-RNA and RNA—RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

The term a "nucleotide sequence" refers to a series of nucleotide bases (also called nucleotides) in a nucleic acid, such as DNA and RNA, and means any chain of two or more nucleotides. In particular, and also noted above, every nucleic acid has a particular nucleotide sequence, which can therefore be used to identify that nucleic acid. A nucleotide sequence includes double or single stranded genomic and cDNA, RNA, any synthetic and genetically manipulated polynucleotide, and both sense and anti-sense polynucleotide. This includes single- and double-stranded molecules, i.e., DNA—DNA, DNA-RNA and RNA—RNA hybrids. This also includes nucleic acids containing modified bases.

The nucleic acids used in accordance with the invention may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage.

Furthermore, the polynucleotides herein may also be modified with a label capable of providing a detectable signal, either directly or indirectly. Exemplary labels include radioisotopes, fluorescent molecules, biotin, and the like. When fluorescently labeled probes are used, many suitable fluorophores are known, including fluorescein, lissamine, phycoerythrin, rhodamine (Perkin Elmer Cetus), Cy2, Cy3, Cy3.5, Cy5, Cy5.5, Cy7, FluorX (Amersham) and others (see, e.g., Kricka, Nonisotopic DNA Probe Techniques, 1992, Academic Press San Diego, Calif.).

Primers

The term "primer", as used herein, also refers to a set of oligonucleotides which provide sufficient sequence variants of the hybridization region to permit hybridization with each member of a given set of target sequence variants, so as to act as a point of initiation of DNA synthesis. Additionally, a primer may consist of one or more oligonucleotides which contain mismatches with some or all members of a given set of target sequence variants, but contains sufficient regions of complementarity with each target sequence variant so as to enable hybridization with all target sequence variants under suitable conditions.

The term "oligonueleotide" refers to a nucleic acid, generally of at least 10, preferably at least 15, and more preferably at least 20 nucleotides and preferably no more than 100 nucleotides, that is hybridizable to a genomic DNA molecule, a cDNA molecule, or an mRNA, or other nucleic acid of interest. Oligonucleotides can be labeled, e.g., with $^{32}P$-nucleotides or nucleotides to which a label, such as biotin or a fluorescent dye (for example, Cy3 or Cy5) has been covalently conjugated. In one embodiment, a labeled oligonucleotide can be used as a probe to detect the presence of a nucleic acid. In another embodiment, oligonucleotides (one or both of which may be labeled) can be used as primers.

Generally, oligonucleotides are prepared synthetically, preferably on a nucleic acid synthesizer. Accordingly, oligonucleotides can be prepared with non-naturally occurring phosphoester analog bonds, such as thioester bonds, etc.

Specific examples of synthetic oligonucleotides include oligonucleotides that contain phosphorothioates, phosphotriesters, methyl phosphonates, short chain alkyl, or cycloalkl intersugar linkages or short chain heteroatomic or heterocyclic intersugar linkages. Most preferred are those with $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—$PO_2$—O—$CH_2$). U.S. Pat. No. 5,637,684 describes phosphoramidate and phosphorothioamidate oligomeric compounds. Also envisioned are oligonucleotides having morpholino backbone structures (U.S. Pat. No. 5,034,506). In other embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone (Nielsen et al., Science 254:1497 (1991)). Other synthetic oligonucleotides may contain substituted sugar moieties comprising one of the following at the 2' position: OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; CF3; OCF3; O—; S—, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substitued silyl; a fluorescein moiety; an RNA cleaving group; a reporter group; an intercalator; a group for improving the pharmacokinetic properties of an oligonucleotide; or a group for improving the pharmacodynamic properties of an oligonucleotide, and other substituents having similar properties. Oligonucleotides may also have sugar mimetics such as cyclobutyls or other carbocyclics in place of the pentofuranosyl group. Nucleotide units having nucleosides other than adenosine, cytidine, guanosine, thymidine and uridine may be used, such as inosine.

A nucleic acid molecule (e.g., primer, oligonucleotide, or probe) is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–9.51). For hybridization with shorter nucleic acids, i.e., oligonucleotides, the position of mismatches becomes more important, and the length of the oligonucleotide determines its specificity (see Sambrook et al., supra, 11.7–11.8).

The primer is a single-stranded DNA. The preferred length of the primer depends on the primer's intended use but typically ranges from 15 to 35 nucleotides. Short primer molecules generally require cooler temperatures to form sufficiently stable hybrid complexes with the template. A primer need not complement the exact sequence of the template but must be sufficiently complementary to hybridize with a template. Primers can incorporate additional features which allow for the detection or immobilization of the primer but do not alter the basic property of the primer, that of acting as a point of initiation of DNA synthesis.

Primers, once hybridized to a nucleic acid sequence (DNA, RNA or DNA-RNA chimeric molecule) that is substantially complementary, may function in amplification methods of the invention as substrates for a polymerase. The 3'OH end of these substrates can be elongated, in the presence of adequate nucleotides and a polymerase, leading to synthesis of a strand complementary to the template sequence on which said primer is hybridized. A primer can also be constituted by hybridizing the end of a single-stranded nucleic acid sequence on itself, leading in particular to formation of hairpin or stem-loop structures.

As used herein, "allele-specific primers" refers to a primer or related sets of oligonucleotides that can be used to detect allelic variations or mutations in the gene.

Computer programs are useful in the design of primers with the required specificity and optimal amplification properties. See, e.g., Oligo version 5.0 (National Biosciences).

Non-Replicable Primers

Non-replicable primers can comprise a single or multiple (in tandem or dispersed in the primer) non-replicable element(s), such as base analog(s), internucleotide extender(s), and/or a cleavable element(s) to name a few. Such non-replicable elements are described in greater detail infra.

Preferably, the non-replicable elements do not interfere with the ability of the primer to initiate chain elongation. Therefore, in the case of many non-replicable elements, they are preferably not located at the terminal residue of any of the primers. The non-replicable element is also preferably located in a position in the primer such that termination at this point will provide no more than an insufficient portion of the binding site of the non-replicable primer.

Preferably, the non-replicable element or elements do not substantially interfere with the primer's ability to efficiently hybridize to its complementary sequence. Those skilled in the art will appreciate that different non-replicable elements may disrupt the ability of a primer to hybridize to a complementary sequence to different extents. For example, 5-nitroindole disrupts the primary structure of the primer less than 1,3-propanediol. In addition, 2'-O-modified RNA blocking groups (a basic ribose groups) may increase the affinity of the primer for its complement. Therefore, primers with a 2'-O-modified RNA group may allow for more efficient primer hybridization. However, as demonstrated in the Examples below, a single 2'-O-methyl ribouracil may not be as efficient in blocking chain elongation as other non-replicable elements, such as 1,3-propanediol. Therefore, it may be preferable to use a primer that has multiple 2'-O-modified RNA groups in tandem or a primer that has a 2'-O-modified RNA group in tandem with a different non-replicable element. For example, in many embodiments it may be preferred to use a primer having a 2'-O-modified RNA residue in tandem with 5-nitroindole. 5-nitroindole may be preferred as a non-replicable element in tandem with other non-replicable elements, such as 2'-O-modified RNA groups, because this base analog generally does not significantly affect the annealing temperature of a primer in which it has been incorporated. Examples of such combinations are described in the Examples below.

In practice, which primer(s) is non-replicable is determined by which strand is preferably amplified. As demonstrated in the Examples below, the product obtained by extension of the replicable primer will be the predominant product of polynomial amplification reactions. Thus, the non-replicable primer hybridizes to an area adjacent to the strand that has the nucleotide sequence of interest and the replicable primer hybridizes to an area adjacent to the strand that has the sequence complementary to the nucleotide sequence of interest.

Base analogs and internucleotide extenders. Chemical groups that can substitute for a nucleotide base are referred to as "base analogs" and "internucleotide extenders." Preferably, such groups, when incorporated into a primer, allow the primer to hybridize to a template and prime synthesis of a complementary nucleic acid, but block nucleic acid replication when incorporated in a template nucleic acid molecule.

Examples of non-replicable base analogs include 2'-deoxyribofuranosyl naphthalene, 5-nitroindole, 2'-O-methyl ribouracil, and other 2'-O modified RNAs, particularly 2'-O-alkyl RNAs. Newton et al. (Nuc. Acids Res. 21: 1155–62 (1993)) describes synthesis of novel base analogs that can be incorporated into oligonucleotides and function as a block for DNA synthesis.

An internucleotide extender is a spacer that joins two segments of the nucleotide and spans one or more nucleotide residues when the two segments are hybridized to a complementary sequence. When the DNA polymerase reaches the internucleotide extender, synthesis is terminated. Examples of internucleotide extenders include 1,3 propanediol (C3 spacer), C12 spacer, S9 spacer, and S18 spacer (Glen Research, Sterling, Va.). Gade et al. (*Genet. Anal. Tech. Appl.*: 10, 61–5 (1993)) discloses the abasic internucleotide extender 1,4-anhydro-2-deoxy-D-ribitol (d-Spacer or abasic ribose). Generally, appropriate spacing with the context of a duplex is achieved with a three-carbon backbone connected to the flanking riboses by phosphate linkages.

Persons skilled in the art(s) of molecular biology and/or DNA chemistry will be able to synthesize primers that contain non-replicable base analogs and internucleotide extenders. For example, primers that contain a residue of 1,3-propanediol can be synthesized according to the method described in Seela et al., *Nuc. Acids Res.* 15, 3113–3129 (1987) and are commercially available, e.g., from Glen Research (Sterling, Va.) and Pierce (Milwaukee, Wis.). Primers containing a residue of 1,4-anhydro-2-deoxy-D-ribitol, the model for the abasic site, can be synthesized according to methods described in Eritja et al., *Nucleosides & Nucleotides* 6, 803–814 (1987). Published European Patent Application No. 416,817 A2 describes the synthesis of primers containing one or more 2' deoxyribofuranosyl naphthalene moieties as non-replicable elements between a primer sequence and a polynucleotide tail. The synthesis of oligonucleotide primers that contain other elements that halt polymerase-dependent copying of the template, such as derivatives of ribonucleosides and deoxyribonucleosides, will be apparent to those who are skilled in the art.

Cleavable elements. A cleavable element is a base residue or multiple base residues which, when cleaved, result in the cleavage of the primer sequence, or a portion thereof, from a primer extension product. Thus, the primer sequence or portion thereof may be effectively removed from a primer extension product before that extension product is itself used as a template in a subsequent primer extension reaction. Therefore, cleavage renders the primer extension product non-replicable; primer extension will terminate at a position such that an insufficient portion of the primer-binding site is present in the product that uses the cleaved product as a template.

One type of cleavable element utilizes the difference in reactivity of phosphodiester bonds adjacent to a ribonucleoside compared with the reactivity of phosphodiester bonds adjacent to deoxyribonucleosides. Primer extension products containing ribonucleotides can be easily cleaved by treating the products with a ribonuclease (RNase), such as mammalian RNase A, *Aspergillus* RNase TI or human RNase H. Mammalian RNase A has the advantage of being thermostabile and cleaving cytidine or uridine residues specifically. *Aspergillus* RNase Ti has the advantage of cleaving guanosine residues specifically. RNase H has the advantage of cleaving RNA only when present in an RNA:DNA duplex, thus assuring that the primer alone will not be cleaved. Human RNase H can cleave a single ribonucleotide, while other RNase H's need multiple ribonucleotides as their substrate.

The sequences that flank either side of the segment of RNA are chosen so as not to be cleaved by the RNase. The sequence's flanking the segment of RNA can be DNA, or RNA in which the 2'-OH group of the sugar is modified to prevent cleavage by RNase. The primer alone is not cleaved, nor is the template strand cut. It is essential that the template strand not be cleaved to allow repeated binding of the primer. The phosphate groups within the flanking sequences can also be modified. It may be preferable to have one or more unmodified DNA residues at the 3' end of the strand to allow for initiation of replication by DNA polymerase. However, if human RNase A is used, then a single ribonucleotide can be incorporated at the 3' end. This terminal ribonucleotide will be able to support primer extension and can be subsequently cleaved by RNase A.

Alternatively, primer extension products containing ribonucleosides can be cleaved by treating the products with a hydroxide, preferably 0.5 N NaOH. Preferred primers will contain one or more ribonucleosides located at a position in the primer so that cleavage will disrupt the hybridization site for one of the primers used in the subsequent primer extension reaction. The ribonucleoside can be located at the 3' terminus of the primer since, unlike the non-replicable element, it will not interfere with the DNA polymerase mediated extension reaction.

If uridine triphosphate (UTP) is incorporated into the primer, the enzyme uracil N-glycosylase (UNG) can also be used to cleave the first primer extension product to remove its complementary primer hybridization site.

The precise chemical nature of the cleavable linkage is not critical. It is important only that this linkage can be cleaved under conditions which do not cleave the DNA synthesized in the extension reaction and that its incorporation into the primer does not interfere with initiation of DNA synthesis. Cleavable internucleotide linkages that can be used in the invention include, but are not limited to, 5'(S)-phosphorothioate and 3'(S)-phosphorothioate linkages and 5'(N)-phosphoramidate and 3'(N)-phosphoramidate linkages. Said phosphorothioate linkages can be cleaved specifically by treatment with silver nitrate or mercuric chloride. Phosphoramidate internucleotide linkages can be selectively cleaved under acidic conditions. As noted above, modified bases such as uridine, which can be converted to an abasic residue (i.e. deglycosylated), can also serve as the cleavable site within the primer. Uridine residues can specifically be converted to abasic sites by treatment with the commercially available enzyme uracil-N-deglycosylase. Cleavage of the primer specifically at such an abasic residue can then be effected under mild alkaline conditions.

Persons skilled in the art(s) of molecular biology and/or DNA chemistry will be able to synthesize primers containing cleavable elements such as those described above. For example, primers containing ribonucleosides can be routinely synthesized by those of skill in nucleic acid chemistry using standard methods of oligonucleotide synthesis by incorporating protected ribonucleotide in place of deoxyribonucleotides in oligonucleotide synthesis reactions known to those of skill in nucleic acid chemistry. Appropriate ribonucleoside containing primers are commercially available.

Nested Primers

A series of nested primers comprises a plurality of primers that are complementary to the same strand. Preferably, the nested primers used in a PA method of the invention are non-replicable primers that do not overlap with one another beyond the position of the non-replicable element.

Preferably, nested primers hybridize to regions adjacent to the nucleotide sequence of interest. A nested primer is able to hybridize to the nucleic acid and to all primer extension products produced by extension of the reverse primer hybridized to a primer extension product of primers upstream of, or 5' to, said nested primer. In the present application, the term "upstream" designates a position 5' to the nucleic acid or the polynucleotide sequence being referred to, and the term "downstream" designates a position 3' to the nucleic acid or said polynucleotide sequence being referred to.

In other words, nested primers are able to hybridize to primer extension products that have terminated upstream of their hybridization site. The nested primers used in the Examples below do not bind to overlapping sequences. However, nested primers that hybridize to overlapping sequences may be used in PA methods of this invention. In practice, the spacing between the nested primers is determined, at least in part, by the spacing of acceptable primer-binding sites adjacent to the nucleotide sequence of interest.

In a preferred embodiment of the invention, all of the primers of the reaction, including the nested primers, are provided in a single reaction mixture. Thus, for each level of nested primers in an amplification reaction to be fully utilized and the maximum amplification yield obtained, it is preferred that the outermost nested primer that is able to bind to the template be utilized in each amplification cycle. Several techniques can be employed in order to promote the outermost primer binding in each reaction cycle. Exemplary methods include:

(1) A polymerase that has 5'-3' exonuclease activity, such as *Thermus acquaticus* or *T. thermophilus*, may be used. The exonuclease activity of the polymerase may then cleave the 5' end of the downstream strand when a forked structure, consisting of a template strand that is duplexed to two daughter strands (in this case, the nested primers and their partial extension products) is present. Such cleavage is followed by ligation of the two strands by the polymerase. Thus, the primer extension product's 5' end begins with the outermost primer.

(2) The process described above in (1) can be modified by having a significantly greater concentration of the outermost primer compared to the other nested primers.

(3) The inner nested primer(s) can also be modified such that they are unable to initiate primer extension until rendered capable to do so. For example, an inner nested primer may have a photolabile-blocking group at its 3' most residue. This photolabile group preferably renders the primer unable to act as a site of primer extension. This group is photolabile and therefore can be removed by light activation. Thus, after a desired number of replication cycles have been performed, the reaction sample can be exposed to light such that the photolabile blocking group is rendered inactive, and thus is able to act as a site of primer extension. An example of a photolabile-blocking group is orthonitrophenyl.

(4) Each level of nested primer could have a less stringent annealing/hybridizing temperature. For example, and not by way of limitation, first, second, and third sets of primers may be provided in a single amplification reaction mixture that prime nucleic acid synthesis at 72° C., 62° C., and 52° C., respectively. Carrying out a first series of primer extension reactions at 72° C. will ensure that only the first primer set will function to bring about primer-dependent nucleic acid synthesis. Following a desired number of cycles, the primer extension temperature can be lowered to 62° C., whereupon the first and second primer sets will prime DNA synthesis. Lowering the primer extension reaction temperature to 52° C. permits all three primer sets to participate in primer-dependent DNA synthesis. Through the use of available, programmable thermal cycling apparatus, all three primer sets as described above can be provided in a single amplification reaction mixture. The primers are selected so that those that prime DNA synthesis under the most stringent conditions bind to the template 3' of the other primers. Similarly, those primers which prime under the least stringent conditions bind to the template 5' of the other primers.

These techniques (i.e., in (1)–(4), supra) can be employed individually or employed in combination with one another so as to assure maximal use of the power of the nested primers. The use of mixtures of primers in the present process permits the process to be carried out in an efficient manner, without the need for the researcher separately to add each primer set as the process progresses. Techniques 1, 2, and/or 3 are preferable to technique 4 because technique 4 decreases the stringency at which the amplification reaction occurs; thus increasing the possibility of anomalous products being produced.

Preferably, the primers of the reaction, including all nested primers, are added to the reaction at the same time. However, nested primers can also be added to the reaction after cycles of amplification have already been performed. Nested primers can also be used in a sequential fashion by which the single-stranded products of a PA reaction can be isolated, purified and then further amplified by a nested primer and the unmodified reverse primer. Rounds of isolation, purification and amplification using different nested primers (and the unmodified reverse primer) can be repeated as many times as desired.

Replication Reactions

Polymerases

Those skilled in the art will appreciate that the present invention can be used with any polymerase suitable for replicating nucleic acids in vitro. Examples of such polymerases include *E. coli* DNA polymerase I, TAQ polymerase, Klenow fragment of *E. coli* DNA polymerase I, T4 DNA polymerase, reverse transcriptase where the template is RNA and the extension product is DNA, or a thermostabile DNA polymerase. Those skilled in the art will also recognize properties that may make the polymerase preferable: such as thermostability and 5'–3' exonuclease activity.

Reaction Conditions

Generally, the DNA synthesis is carried out in the presence of four different nucleoside triphosphates and an agent for polymerization (e.g., DNA polymerase or reverse transcriptase) in an appropriate buffer (e.g., Tris-HCl), and at suitable temperatures (e.g., at an annealing temperature of from about 45° C. to about 85° C.; at an extending temperature of from about 55° C. to about 75° C.; and at a denaturing temperature of about 95° C.). Standard amplification conditions are known in the art and are described for example in Ausubel, supra (see, in particular, Chapter 15).

The nucleic acid sequence of interest may encompass essentially the entire length of the template strand(s), or it may comprise only a very minor portion of it. The template strand(s) containing the sequence of interest may be present in a substantially homogeneous sample or as part (even an extremely minor part) of a mixture of nucleic acids.

In some cases, it may be desirable to first make multiple copies of the target sequence using a linear amplification reaction. In a linear amplification reaction, a single primer is used and only one strand is copied. The product can be isolated on a solid support using an affinity group attached to the primer, such as biotin, or by hybridization to an immobilized nucleic acid fragment complementary to a portion of the desired extension product. Cell debris and other impurities as well as the background DNA are washed away. After release of the target sequence from the support, PA can be done. Such a procedure can be done, for example, when it is desired that only the strand being amplified, and not its complement, will be present during the PA reaction.

The primers are permitted to anneal to their respective starting templates, and are extended in the presence of a polymerase enzyme, under conditions appropriate for the function of the enzyme, to form first generation primer extension products. The process may be repeated, e.g., by denaturing the resulting duplexed nucleic acid, permitting the primers to anneal to the strands and again carrying out the primer extension reaction.

It may be preferable to first make multiple copies of the target sequence by performing multiple cycles, preferably 10–20 cycles, of PCR and then performing PA. This embodiment may be particularly preferable in instances when a very low copy number of a sequence to be amplified is present in a sample.

It is known that primer-binding conditions, especially temperature, can dictate whether a specific primer will bind to a specific template. See Rychlik et al., *Nuc. Acids Res.* 18, 6409–6412 (1990) (herein referred to as "Rychlik"); Wu et al., DNA Cell Biol. 10, 233–238 (1991) (herein referred to as "Wu"). Thus, in a reaction mixture containing primers of various base composition and/or lengths, the selection of a primer binding temperature can also function to select which primers will be capable of priming DNA synthesis.

The optimal reaction conditions for polynomial amplification may vary slightly from those typically used in amplification reactions that do not use non-replicable primers. The non-replicable elements may require that the primer annealing temperature be raised or lowered. For example, with the base analog 1,3-propanediol, an annealing temperature of 55° C. is typically advantageous over 60° C. In addition, the reactions may proceed better when the concentration of magnesium is higher than 1.5 mM (such as 3.5 mM or 5 mM).

The design of primers that bind at preselected temperatures is within the skill of molecular biologists. The temperature at which a specific primer will function can be predicted by available algorithms (Wu et al., *DNA Cell Biol.* 10, 233 (1991)) and by computer programs (Rychlik et al., *Nucleic Acids Res.*, 1, 6409–6412 (1990)), based upon primer length and base composition. The presence of non-replicable elements in a primer also needs to be taken into account when calculating primer-annealing temperature. For example, C3 spacers lower the optimal annealing temperature, 2'-O-modified RNAs slightly increase optimal annealing temperature, and 5'-nitroindole essentially does not change optimal primer anneal temperature. Replicable primers may be shortened or lengthened so as to "match" the lower or higher annealing temperature of the non-replicable primers.

In the case that the starting nucleic acid is double-stranded, the conditions such that a first generation product that is capable of hybridizing to the replicable primer is produced includes an initial heating step to separate the strands. The primer(s) are added either prior to or following denaturation of the template. If the starting nucleic acid is double stranded, there will implicitly be two primer extension products generated initially: one generated by extension of the non-replicable primer and the other generated by the extension of the replicable primer.

Primer extension products can be separated from their respective template by heating the sample. For example, extension products can be separated by heating at 95° C. Appropriate temperature cycling for in vitro DNA amplification can be performed manually or by commercially available, programmable thermal cycler apparatus. Very fast cycle times can be achieved using hot air cyclers (Wittwer et al., *Nuc. Acids Res.* 17, 4353–4357 (1989)); cycle times as short as thirty seconds are possible (Wittwer et al., *Biotechniques* 10,76–83 (1991)). Thus, one hundred cycles of primer extension can be achieved in as little as about fifty minutes.

Alternatively, amplification systems in which the reaction sequence described above occurs continuously under a constant set of conditions can be used. These systems offer two important advantages. First, the need to oscillate the temperature of the reaction conditions is eliminated, simplifying the procedure. Secondly, the effective cycle time is reduced, leading to a higher level of amplification.

For example, extension products can be separated from their respective template, without the use of heat, by strand displacement. Cleavable primers and rolling-circle amplification are two examples of techniques employing strand displacement. Isothermal amplification techniques are well known in the art (see for example, U.S. Pat. Nos. 5,455,166; 5,824,517; 6,214,587; and 6,251,639 and Walker et al. *Nuc. Acid. Res.* 20;7: 1691–1696 (1992)).

Reaction Product

The primary products of the amplification process of the present invention are preferably single-stranded synthetic DNA's of a defined length. A user skilled in the art of nucleic acid amplification will be able to determine the length or size of a particular amplification product based on the nucleic acid sequence being amplified and the location of the primer(s) with respect to that sequence.

Detection. The products can be detected by known nucleic acid detection techniques, including the use of primers or probes labeled with radioactivity, a fluorescent moiety or an enzyme, an ultraviolet absorbing stain etc., electrophoresis, high pressure liquid chromatography, etc. Another method for determining if amplification has occurred involves testing a portion of the amplified reaction mixture for ability to hybridize to a labeled probe designed to hybridize only to the amplified DNA.

Purification. Methods for purifying nucleic acids are well known in the art. For example, nucleic acids can be purified by precipitation, chromatography (including without limitation preparative solid phase chromatography, oligonucleotide hybridization, and triple helix chromatography), ultracentrifugation, and other means. In one particular embodiment of the invention, a primer used in the PA reaction comprises a purification handle that is used for purification of the reaction product, or particular amplification products. As used herein the "purification handle" is any tag or group on the nucleic acid used to aid in its purification. Examples of purification handles include, inter alia, members of high-affinity binding pairs such as biotin. PA products can also be purified by hybridization to a complementary nucleic acid sequence.

Many of the purification methods known in the art require the use of a solid phase support. For use in the present invention the solid phase support will be inert to the reaction conditions for binding. As used herein, a solid phase support is not limited to a specific type of support. Rather a large number of supports are available and are known to one of ordinary skill in the art. Solid phase supports include silica gels, resins, derivatized plastic films, glass beads, cotton, plastic beads, alumina gels, magnetic beads, membranes (including but not limited to nitrocellulose, cellulose, nylon, and glass wool), plastic and glass dishes or wells, etc. For example, solid phase supports used for peptide or oligonucleotide synthesis can be used, such as polystyrene resin (e.g., PAM-resin obtained from Bachem Inc., Peninsula Laboratories, etc.), POLYHIPE" resin (obtained from Aminotech, Canada), polyamide resin (obtained from Peninsula Laboratories), polystyrene resin grafted with polyethylene glycol (TentaGel", Rapp Polymere, Tubingen, Germany) or polydimethylacrylamide resin (obtained from Milligen/Biosearch, California). In synthesis of oligonucleotides, a silica based solid phase support may be preferred. Silica based solid phase supports are commercially available (e.g., from Peninsula Laboratories, Inc.; and Applied Biosystems, Inc.).

Applications

The present invention will have important utility in the detection of nucleic acid sequences, with applications such as the detection of mutations associated with genetic diseases, the detection of pathogens such as viruses and bacteria, allelic discrimination by genotyping, and the detection and quantification of the expression for one or more genes.

One particular area of importance is in the diagnosis of human and other animal genetic diseases. Many human genetic diseases are known to be caused by specific changes, or mutations, in genes of known sequence. For these specific mutations, DNA-based diagnosis is possible using hybridization or other allele specific technologies to determine which of the various gene sequences are present in the DNA of a person at risk for the disease(s). Clearly, amplification of target DNA has been very helpful in developing these technologies. The advantages of template amplification include: smaller sample sizes can be used, the signal to noise ratio of the detection system is improved, there is a real potential for automation and the amplification system itself can be the detection system. PA can be performed directly on a genomic sample, rapidly providing an abundant, sterile product that can be used immediately for genotyping the subject.

For example, PA can be used to detect and diagnose viral infections, particularly viral infections characterized by very low levels of viral nucleic acids, such as HIV infection. In a specific embodiment, reverse transcriptase-initiated PA is used to detect the level of expression of HIV mRNA. Using a sensitive amplification system amenable to high levels of amplification, such as PA, is vital; in some cases, less than 1 in 1000 to 10,000 cells in a sample may be infected with HIV. Oligonucleotide primers corresponding to sequences of HIV mRNA can be prepared for use as primers. Sequences for such oligonucleotide primers are readily available from the information known about HIV genomic sequences. The oligonucleotides may be utilized as primers to amplify by PA mRNA obtained from peripheral blood cells. Other, exemplary viruses that may be detected in such amplification methods include hepatitis C virus (HCV), hepatitis B virus (HBV), cytomegalovirus (CMV), Epstein Barr Virus (EBV), and Parvovirus B19, to name a few.

PA can also be used to detect and quantify the presence of an RNA. In a preferred embodiment, the expression level of a gene is determined by the levels of its RNA. For example, to test for the presence of a particular mRNA in a sample, the sequence of interest can be reverse transcribed and then PA can be performed on the product of the reverse transcription reaction. Such a combination of reverse transcription and PA can be done in a manner such that expression levels can be quantitated.

In general, PA may be used as part of any method or technique where nucleic acid molecules are amplified, including known techniques where traditional amplification methods (e.g. PCR) are normally used. However, PA has important advantages over other amplification techniques. For example, PA is much less susceptible to false-positive results than PCR. The products of PA are sterile, that is, unable to serve as templates for replication. Therefore, these products cannot contribute to carry-over contamination. This property is particularly important when performing diagnostic tests because minimizing false-positive results is crucial in diagnostics.

An additional advantage of PA is that its product is predominantly single-stranded. Single-stranded products are immediately available for a wide array of hybridization and sequencing reactions. The preferential amplification of one strand is particularly helpful when the sequence of each strand is to be determined. For example, when identifying single nucleotide polymorphisms (SNPs), which can serve as a marker for a disease-causing mutation, it is important to confirm that the polymorphism is located on both strands of the nucleotide sequence. Therefore, two different sets of primers can be designed that amplify each of the strands and the product of these two PA reactions can be used to sequence the SNP region of interest.

"Sequencing" as used herein includes, inter alia, chemical sequencing of DNA (also known as Maxam-Gilbert sequencing; see, Maxam & Gilbert, *Proc. Natl. Acad. Sci. USA* 1977, 74:560), as well as enzymatic sequencing of DNA (Sanger et al., *Proc. Natl. Acad. Sci.* USA 1977, 74:5463, 1977).

In some instances, such as when there is a particularly low copy number of the starting sequence of interest, it may be preferable to perform a small number of cycles, such as 10–20 cycles, of PCR and then perform PA. PCR followed by PA would combine the replicative power of PCR with the ability of PA to minimize the risk of generating products that can serve as a source of carry-over contamination. A combination of PCR and PA could be performed by doing PCR with a set of primers and then raising the temperature so that one of the replicable primers, which cannot operate at a specified higher temperature, could not participate in the PA portion of the reaction.

The same properties described above that make PA advantageous for diagnostic purposes—sensitivity, amplification power, single-stranded product, and low-risk of carry-over contamination—make it equally advantageous for applications such as forensic nucleic acid analysis and genotyping.

In one embodiment of the present invention, a primer is designed such that its 3' nucleotide is complementary to a particular nucleotide in the template known to be variable (polymorphic). The variable nucleotide can be a nucleotide involved in a genetic disease such as sickle cell anemia, or at another site known to be polymorphic.

If a mismatch is present between the 3' nucleotide of the primer and the corresponding nucleotide of the template DNA, the primer design insures that it will be extended poorly, or, preferably, not at all. See Petruska et al., *PNAS U.S.A.* 85, 6252–6256 (1988). Thus, such a primer is "allele specific" and capable of discerning the presence of absence of a single base within a nucleic acid sequence of interest. The presence of synthetic DNA following the use of an allele-specific primer in the process according to the present invention thus is indicative of the presence of the allele of interest in the original DNA template.

This allele-specific characteristic of oligonucleotide priming has been used to perform allele-specific PCR. See, for example, Newton et al., *Nucleic Acids Res.* 17, 2503–2516 (1989). As is the case with PCR in general, however, the exponential behavior of the allele-specific PCR reaction has been associated with difficulties in running the reaction (see, Ugozzoli et al., *Methods* 2, 42–48 (1991)). However, the polynomial features of the present amplification process, due to the presence of a non-replicable element or elements within the allele-specific primer(s), avoids such difficulties.

The PA product can also be used as a tool in and of itself. For example, a known sequence can be amplified by PA in order to generate a probe of a particular sequence. In an embodiment of the invention, labeled dNTPs, such as radiolabelled or fluorescently labeled dNTPs, are added to the amplification reaction. Thus, the resulting product will be readily detectable and can be used as a probe in hybridization techniques.

As used herein, the term "probe" refers to an oligonucleotide that forms a duplex structure with a sequence of a target nucleic acid encodes a due to complementary base pairing. The probe will contain a hybridizing region, which is a region of the oligonucleotide corresponding to a region of the target sequence. A probe oligonucleotide either can consist entirely of the hybridizing region or can contain additional features that allow for the detection or immobilization of the probe but do not alter the hybridization characteristics of the hybridizing region. The term "probe" also refers to a set of oligonucleotides that provide sufficient sequence variants of the hybridization region to permit hybridization with each member of a given set of target sequence variants. Additionally, a probe can contain mismatches with some or all members of a given set of target sequence variants, provided that it contains sufficient regions of complementarity with each target sequence variant to permit hybridization with all target sequence variants under suitable conditions.

Kit. In a preferred embodiment of the invention, the reagents necessary to apply PA to diagnostics, forensics, and genotyping, can be provided in a kit. The present invention also provides such reagent kits for use in amplifying a particular nucleic acid sequence. Such a kit will typically contain a DNA polymerase and two or more primers for each sequence to be amplified wherein at least one of said primers comprises a non-replicable element and one primer is replicable. Optionally, the kit may also contain a control nucleic acid sequence capable of being replicated by the primers and DNA polymerase. The replicable primer may be labeled. The kit also may contain a nucleic acid probe capable of indicating the presence or absence of an amplification product of the particular sequence. Where the kit contains primers incorporating a cleavable element, it may also contain reagents for cleaving the primer at the cleavable element.

EXAMPLES

The invention is also described by means of the following particular examples. However, the use of these and other examples in the specification is illustrative only and in no way limits the scope and meaning of the invention or of any exemplified term. Likewise, the invention is not limited to any of the preferred embodiments described or exemplified herein. Indeed, many modifications and variations of the invention will be apparent to those skilled in the art upon reading this specification and can be made without departing from its spirit and scope. The invention is therefore to be limited only by the terms of the appended claims along with the full scope of equivalents to which the claims are entitled.

Example 1

Mathematical Analysis of Polynomial Amplification Scheme With Comparison to Linked-Linear Amplification For the purpose of a more controlled comparison, assume that each parent only produces one child every cycle. This assumption is consistent with those made of both standard PCR as well as the LLA amplification scheme.

For our purposes, let the function $x_k(n)$ refer to the amount of the kth product produced in the reaction after the nth reaction cycle.

The amount of a product after a given cycle in both the polynomial amplification scheme as well as the LLA scheme can be calculated recursively as the sum of the amount of the kth product from the previous cycle, $x_k(n-1)$, plus the amount of the product that produces it that was present in the previous cycle, $x_k-1(n-1)$. This gives us the recursive definition of our function $$x_k(n) = x_k(n-1) + x_{k-1}(n-1) \tag{1}$$

for k>1. Also, we note that $x_1(n)=1$ for all n, since we only have 1 pair of our original parent strands throughout the reaction. Secondly, note that $x_k(n)=1$ when n=k, since the first instance of the kth product is not created until the kth cycle.

Now, consider Pascal's triangle (or at least the first 7 rows of it):

```
         1
        1 1
       1 2 1
      1 3 3 1
     1 4 6 4 1
    1 5 10 10 5 1
   1 6 15 20 15 6 1
  1 7 21 35 35 21 7 1
```

One of the hallmarks of this structure is how each number in the triangle is recursively generated by the pair of numbers directly above it. More specifically, if $P_k(n)$ is the kth number in the nth row of the triangle, then the value of $P_k(n)$ is given by the sum of the kth and the (k−1)th numbers in the previous row. In other words, $$P_k(n) = P_k(n-1) + P_{k-1}(n-1)$$

Now, we see also that $p_1(n)=1$ for all n, and $p_k(n)$ 1 when n=k. This, however, is the same as the recursive formula for both the polynomial amplification scheme as well as LLA, along with the same initial conditions. Thus, it stands to reason that any closed form expression that generates the kth number in the nth row of Pascal's triangle will also generate the amount of the kth product after n cycles for the amplification schemes.

As it turns out, such as closed form expression does exist. One formula that determines the value of the kth element in the nth row of Pascal's triangle is (Read: n choose k), which is defined as $$\binom{n}{k}$$

(Read: n choose k), which is defined as $$\binom{n}{k} = \frac{n!}{k!(n-k)}$$

Now, if we wish to find a closed form expression for the growth of the kth product in the amplification schemes, we can hold k fixed, and we see $$x_k(n) = \binom{n}{k}$$

$$= \frac{n!}{k!(n-k)}$$

$$= \frac{n(n-1) \ldots (n-k+1)(n-k)(n-k-1) \ldots (1)}{k!(n-k)(n-k-1) \ldots (1)}$$

$$= \frac{n(n-1) \ldots (n-k+1)}{k!}$$

Note that the numerator of this fraction contains k terms, so for a given value of k, the order of the polynomial is k. Thus, the growth of the kth product for both the polynomial amplification scheme and LLA is determined by a polynomial of order k. Also, if a shift is required in order to properly fit the cycle-for-cycle count of a particular product in the given scheme, this can be achieved by replacing n with n−c, where c is an integer constant that corresponds to the number of cycles a particular product needs to be shifted to model the data.

This transformation, however, does not change the leading coefficient, or the order of the polynomial being used to describe the growth of the product. Therefore, as the number of cycles grows arbitrarily large, there is no difference in the growth rate between a shifted and a non-shifted description of a particular product.

In the LLA amplification scheme, both the forward and reverse primers are blocked, and two complementary strands are produced that cannot support priming by either of the primers present. Thus, for each order of nesting m, the final product is the (m+2)th one produced, and thus the amount of the final product after n cycles will be approximately equal to $$\frac{n^{m+3}}{(2m+3)!}$$

Now, for each order m of nesting in the "polynomial" amplification scheme, there are two new products produced: a sense strand that forms when the new nested forward primer binds to the formerly sterile product from the previous order of nesting, and the new sterile antisense product that forms from the reverse primer binding and ex-tending off of the new sense strand. Thus, the final sterile product is the (2 m+3)th product produced. As such, the amount of the final product after n cycles will be approximately given by $$\frac{n^{m+3}}{(2m+3)!}.$$

Thus, for each added nesting, the order of the polynomial describing the growth of the polynomial amplification scheme of the invention increases by 2, whereas the order of the polynomial describing the growth of LLA only increases by 1. Thus, it would require 12 nestings (26 primers) to obtain the amplification level of $3.44E^{10}$ products in 35 cycles, polynomial amplification requires only 5 nestings (7 primer system). From this we see that LLA only increases one order of magnitude with each nesting. To get the same $7^{th}$ order amplification of polynomial amplification (2 nestings, 3 for and 1 rev), LLA would require 6 nestings or 7 sets of forward and reverse blocked primers (14 blocked oligos).

The comparison between polynomial amplification and LLA is that LLA increases only a single order of magnitude for each subsequent nesting, beginning at a linear rate with no nesting, while requiring more than three times the number of primers of polynomial amplification when nesting. Polynomial amplification increases at a rate of 2 orders of magnitude with each nesting beginning at $n^3/3!$ with no nesting, thus LLA must have two orders of nesting to obtain the level of polynomial amplification with no nesting. Thus, the polynomial amplification system is more robust and cost effective compared to the LLA system.

Example 2

Choice of Non-Replicable Group Used in Primers

In polynomial amplification, DNA synthesis in one direction must initiate from an oligonucleotide primer that has been modified with a group that blocks the ability of that oligonucleotide to support DNA synthesis itself as a template (a non-replicable group) (by convention, the blocked primer will be "forward" orientation hereafter). The "reverse" primer is not blocked and can be an unmodified DNA oligonucleotide. It is important that the blocking group(s) inhibit DNA polymerase processivity, as products that extend through the block will affect the behavior of the amplification system.

A series of different modifying groups were inserted into a synthetic DNA template and tested for their ability to block DNA synthesis in a primer extension reaction under direct and cycling conditions.

Materials and Methods

Thirteen template oligonucleotides and 1 primer oligonucleotide were synthesized using solid-phase phosphoramidite chemistry (Caruthers et al., 1992) and are shown in Table 3. Internucleotide extenders are indicated as follows: "n" represents the C3-Spacer (1,3-propanediol, Spacer Phosphoramidite C3; Glen Research, Sterling, Va.) and "d" represents 1,4-anhydro-2-deoxy-D-ribitol (d-Spacer CE phosphoramidite; Glen Research, Sterling, Va.). Nucleotide analogs are indicated as follows: "y" represents 5-nitroindole (5-Nitroindole-CE phosphoramidite; Glen Research, Sterling, Va.), "u" represents 2'-O-methyl uracil, and "c" represents 2'-O-methyl cytosine bases (betacyanoethyl phosphoramidite; Pierce, Milwaukee, Wis.). The Primer oligonucleotide is aligned below the unmodified control sequence.

Template oligonucleotides were purified by polyacrylamide gel electrophoresis (PAGE). Template oligonucleotides included an unmodified control (SEQ ID NO: 2) and 12 oligonucleotides having either 1 or more internal modifying group(s) that were tested for their capacity to block DNA synthesis (SEQ ID Nos. 3–10 and 31–34).

TABLE 3

| Template Sequences | Modification | Seq. Identity |
|---|---|---|
| 5' ACTTTAGCGATAGTCTyynGCGTTATGCATTTTGCTGCCGGTCAC 3' | 1x C3 + 2x 5-NI | SEQ ID NO: 34 |
| 5' ACTTTAGCGATAGTCTTynGCGTTATGCATTTTGCTGCCGGTCAC 3' | 1x C3 + 1x 5-NI | SEQ ID NO: 33 |
| 5' ACTTTAGCGATAGTCTTnnGCGTTATGCATTTTGCTGCCGGTCAC 3' | 2x C3-Spacer | SEQ ID NO: 10 |
| 5' ACTTTAGCGATAGTCTTTnGCGTTATGCATTTTGCTGCCGGTCAC 3' | 1x C3-Spacer | SEQ ID NO: 9 |
| 5' ACTTTAGCGATAGTCTTddGCGTTATGCATTTTCCTGCCCGTCAC 3' | 2x d-Spacer | SEQ ID NO: 8 |
| 5' ACTTTAGCGATAGTCTTTdGCGTTATGCATTTTGCTGCCGGTCAC 3' | 1x d-Spacer | SEQ ID NO: 7 |
| 5' ACTTTAGCGATAGTCTTyyGCGTTATGCATTTTGCTGCCGGTCAC 3' | 2x 5-Nitroindole | SEQ ID NO: 6 |
| 5' ACTTTAGCGATAGTCTTTyGCGTTATGCATTTTGCTGCCGGTCAC 3' | 1x 5-Nitroindole | SEQ ID NO: 5 |
| 5' ACTTTAGCCATAcucuuuuCCGTTATCCATTTTGCTGCCGGTCAC 3' | 6x 2'-O-Methyl RNA | SEQ ID NO: 32 |
| 5' ACTTTAGCGATAGTCuuuuGCGTTATCCATTTTGCTGCCGGTCAC 3' | 4x 2'-O-Methyl RNA | SEQ ID NO: 31 |
| 5' ACTTTAGCGATAGTCTTuuGCGTTATGCATTTTGCTCCCGGTCAC 3' | 2x 2'-O-Methyl RNA | SEQ ID NO: 4 |
| 5' ACTTTAGCGATAGTCTTTuGCGTTATGCATTTTGCTGCCGGTCAC 3' | 1x 2'-O-Methyl RNA | SEQ ID NO: 3 |
| 5' ACTTTAGCGATAGTCTTTTGCGTTATGCATTTTGCTGCCCGGTCAC 3' | None (Control) | SEQ ID NO: 2 |
| ::::::::::::::::::: | | |
| 3'                        ← GTAAAACGACGGCCAGTG 5'<br>Primer | | SEQ ID NO: 1 | u = 2'-O-methyl uracil
c = 2'-O-methyl cytosine
n = C3-Spacer
y = 5-nitroindole
d = d-Spacer The primer oligonucleotide was radiolabeled using γ-$^{32}$P-ATP and polynucleotide kinase as described (Sambrook and Russell, 2001). Labeling reactions incubated for 1 hour at 37° C. and comprised:

TABLE 4

Kinase Labeling Reaction.

- 5 pmoles DNA oligonucleotide
- 70 mM Tris, pH 7.6
- 10 mM MgCl$_2$
- 5 mM DTT
- 50 uCi gamma-32P-ATP (6000 Ci/mmol, Amersham, Piscataway, NJ)
- 5 units T4 Polynucleotide kinase (New England Biolabs, Beverly, MA)
- 50 µl final volume Following incubation, unincorporated radionucleotides were separated from the reaction products by passage through a Sephadex G25 spin column twice. Radiolabel incorporation was measured by scintigraphy on a Packard Tri-Carb 1900CA Scintillation Analyzer (Packard Bioscience, Meriden, Conn.).

Primer extension reactions first tested using equal amounts of primer and template nucleic acids in a single step reaction with incubated at 95° C. for 1 minutes, 50° C. for 15 minutes, and 72° C. for 15 minutes. Reactions were 20 µl final volume and comprised:

TABLE 5

Primer Extension Reaction Conditions.

- 10 mM Tris pH 8.3
- 50 mM KCl
- 2.5 mM MgCl$_2$
- 1 mM dNTPs
- 50 nM template oligonucleotide
- 50 nM cold primer oligonucleotide
- 20,000 CPM 32P-labeled primer oligonucleotide
- 5 units Amplitaq ™ DNA polymerase (Applied Biosystems Inc., Foster City, CA)

Figure 5:
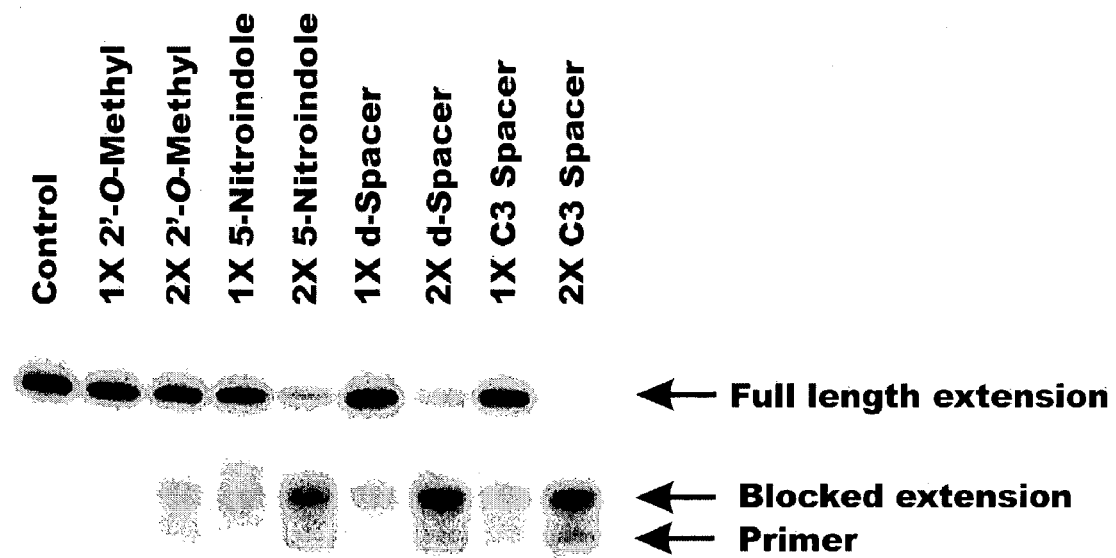
FIG. 5. Capacity of various DNA modifying groups to block template function of oligonucleotides in a primer extension assay. A 5'-32P labeled oligonucleotide was used to prime DNA synthesis on various templates outlined in Table 3 (SEQ ID NOS: 2–10). Primers and template were present at equal molar concentrations and the reaction was incubated without cycling. Reactions products were separated using PAGE and visualized using scintigraphy. Position of the unreacted primer (18-mer), blocked extension products (26-mer), and full-length extension products (45-mer) are indicated.

The primer extension reactions were stopped with the addition of an equal volume (20 ul) of 2× gel loading buffer (7 M urea, 100 mM EDTA). Stopped reactions were denatured for 5 minutes at 95° C. and cooled on ice. Reaction products were evaluated by polyacrylamide gel electrophoresis (PAGE). Half of each reaction was loaded onto a 12% acrylamide, 7M urea, 0.5× TBE (45 mM Tris-borate, 1 mM EDTA) gel and run for 2 hours at 100 volts. The gel was exposed to a Packard MP phosphor screen for 2 hours and visualized using a Packard Cyclone™ Storage Phosphor System (Packard Biosciences, Meriden, Conn.) and is shown in FIG. 5.

Figure 6:
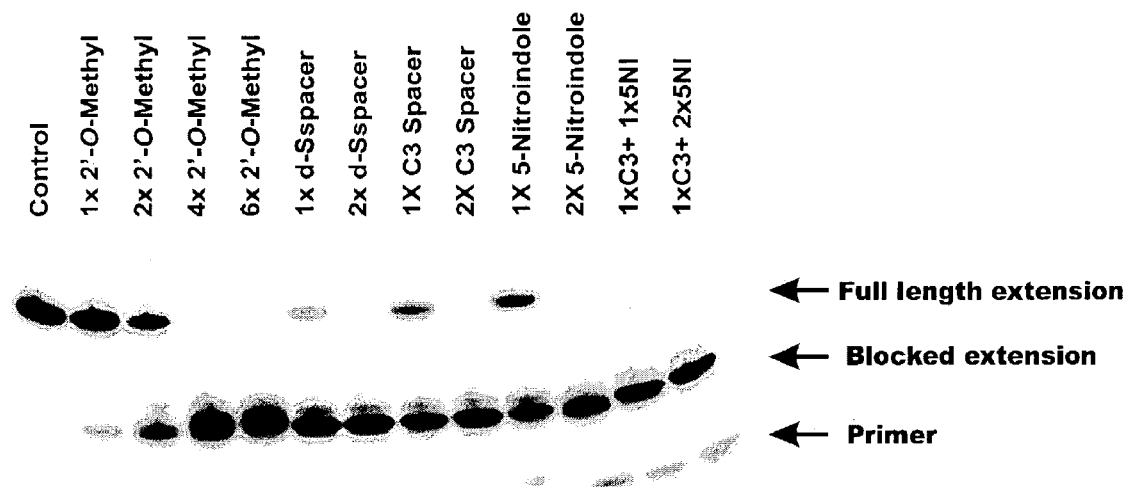
FIG. 6. Capacity of various DNA modifying groups to block template function of oligonucleotides in a cycling primer extension assay. A 5'-32P labeled oligonucleotide was used to prime DNA synthesis on various templates outlined in Table 3 (SEQ ID NOS: 2–10 and 31–34). Template nucleic acids were present at 1/10 the concentration of primer nucleic acids. The reaction was incubated with 20 rounds of thermal cycling to simulate an amplification reaction. Reactions products were separated using PAGE and visualized using scintigraphy. Position of the unreacted primer (18-mer), blocked extension products (26-mer), and full-length extension products (45-mer) are indicated.

In a second set of experiments, primer extension reactions were tested using primer excess and the reactions were cycled, to better simulate the setting of an amplification reaction. Reaction mix was identical to that described in Table 5 except template nucleic acids were reduced by 10-fold to 5 nM final concentration. Reactions were incubated at 95° C. for 1 minute then cycled for 20 steps of 95° C. for 30 seconds, 50° C. for 30 seconds, and 72° C. for 30 seconds. Reactions were stopped and evaluated by gel electrophoresis and scintigraphy as before. Results are shown in FIG. 6.

Results and Discussion

In the primer extension reactions, the 18-mer primer oligonucleotide will be elongated by Taq DNA polymerase to yield a truncated 26-mer product if the modifying group(s) successfully block DNA synthesis or, alternatively, will yield a full-length 45-mer product if the modifying group(s) do not block DNA synthesis. Results of single-step primer extension reactions are shown in FIG. 5. Reaction products using both of the 2'-O-methyl RNA modified templates (SEQ ID NOS: 3 and 4) extend to the full-length 45-mer, indicating that this group does not effectively block Taq DNA polymerase. Reaction products using any of the templates with a single modified blocking group (SEQ ID NOS: 5, 7, and 9) mostly extend to full length. Templates having 2 modified sites were more effective in blocking DNA polymerase activity; tandem insertions of 5-nitroindole (SEQ ID NO: 6) is somewhat effective, tandem insertions of d-Spacer (SEQ ID NO: 8) is more effective, and tandem insertions of C3 Spacer (SEQ ID NO: 10) is entirely effective in blocking DNA polymerase activity. The reaction conditions employed herein provide long incubation periods, large amounts of template, and excess polymerase.

Blocking capacity of the various groups may be more effective in an actual amplification reaction where rapid cycling occurs and template concentration is very low (at least initially).

Results of 20-cycle primer extension experiments with reduced template concentration is shown in FIG. 6. Under these conditions, blocking potency of each group was enhanced. All double-modified templates (except 2'-O-methyl RNA) were effectively blocked. The 2'-O-methyl RNA modification totally blocked with 4 insertions.

Although use of a single blocking group impedes replication DNA polymerase processivity, use of two blocking groups in tandem is more effective. Of the modifying groups tested, the C3 Spacer was most effective in blocking DNA polymerase. However, insertion of multiple spacer groups, like the C3 Spacer, can disrupt the cooperative base stacking interactions that stabilize normal duplex DNA, can decrease $T_m$, and might interfere with priming function of the modified oligonucleotide. Modified bases such as 2'-O-modified RNA or 5-nitroindole do not interfere with primer hybridization and contribute favorably to base stacking interactions. Use of mixed modifiers, such as insertion of a C3 Spacer and a 5-nitroindole in tandem, provide effective blocking function while being less disruptive to primer hybridization than insertion of multiple spacer groups.

The experiments shown in FIGS. 5 and 6 demonstrate that use of two non-replicable elements inserted in tandem results in significantly greater blocking efficiency than use of a single non-replicable element. Use of blocked primers with single base analog blocking groups could result in primer-extension read-through (i.e., full-length extension products), which could lead to an exponential amplification cascade (i.e., PCR), instead of the desired reaction. Evidence for the existence of such "read-through" species for single-blocked templates is demonstrated in Example 3.

Example 3

Greater Amplification Rate for the Reverse-Strand Product

Amplification reactions conducted using the method of the invention accumulate (i.e., amplify) specific reaction products derived from the target (template) nucleic acid. Products made from the unmodified primer will accumulate faster than products made using modified blocked primer(s). Amplification products were examined using radiolabeled primers to determine if strand accumulation favors products made from the unmodified primer as predicted by mathematical modeling of polynomial amplification (as described in Table 8 and Example 1).

Materials and Methods

Nucleic acids. A synthetic amplicon was employed as a model system to test properties of the new amplification method. As used herein the term "amplicon" is an amplification reaction product defined by a set of forward and reverse primers on a known template. A 195 base-pair (bp) fragment of the rat Cyclophilin gene (Genbank M19533, locus RATCYCA) was cloned into the pCR11-TOPO vector (Invitrogen, Carlsbad, Calif.), and is hereafter referred to as the "Rat CP gene target" (SEQ ID NO: 11). Primer oligonucleotides were synthesized specific for the Rat CP gene target that included unmodified primers (in both the forward and reverse orientation) as well as primers modified with various blocking groups (forward orientation only). Primers are shown in Table 6. Relative positioning of the primers and the probe within the Rat CP gene target are shown in FIG. 7. The probe, SEQ ID NO: 30 (5' 6FAM-CGCGTCTGCT-TCGAGCTGTTTGC-BH1 3') has a 6-carboxyfluorescein (6Fam) label at its 5' end and a Black Hole Quencher™ 1 (BH1) at its 3' end. Primers were designed to allow for both PCR amplification as well as direct (2 primer) and nested (3 primer) polynomial amplification using the method of the invention.

Table 6

Primer Oligonucleotides for Rat CP Amplicon.

| Sequence | Modifying Group | Identity | Primer Site |
|---|---|---|---|
| ACGACTCACTATAGACATGGTCAAC | None | SEQ ID NO: 12 | For-1 |
| ACGACTCACTATAGACATyGTCAAC | 1x 5-nitroindole | SEQ ID NO: 13 | For-1 |
| ACGACTCACTATAGACAyyGTCAAC | 2x 5-nitroindole | SEQ ID NO: 14 | For-1 |
| ACGACTCACTATAGACATnGTCAAC | 1x C3 Spacer | SEQ ID NO: 15 | For-1 |
| ACGACTCACTATAGACAnnGTCAAC | 2x C3 Spacer | SEQ ID NO: 16 | For-1 |
| ACGACTCACTATAGACAynGTCAAC | 1x C3 Spacer 1y 5-nitroindole | SEQ ID NO: 17 | For-1 |
| ACGACTCACTATAGACyynGTCAAC | 1x C3 Spacer 2y 5-nitroindole | SEQ ID NO: 18 | For-1 |
| CCACCGTGTTCTTCGACATC | None | SEQ ID NO: 19 | For-2 |
| CCACCGTGTTCTTyGACATC | 1x 5-nitroindole | SEQ ID NO: 20 | For-2 |
| CCACCGTGTTCTyyGACATC | 2x 5-nitroindole | SEQ ID NO: 21 | For-2 |
| CCACCGTGTTCTTnGACATC | 1x C3 Spacer | SEQ ID NO: 22 | For-2 |
| CCACCGTGTTCTnnGACATC | 2x C3 Spacer | SEQ ID NO: 23 | For-2 |
| CCACCGTGTTCTynGACATC | 1x C3 Spacer 1y 5-nitroindole | SEQ ID NO: 24 | For-2 |
| CCACCGTGTTCyynGACATC | 1x C3 Spacer 2y 5-nitroindole | SEQ ID NO: 25 | For-2 |
| ATGGCGAGCCCTTGGG | None | SEQ ID NO: 26 | For-3 |
| GATCCACGTTATGTCGGAGTG | None | SEQ ID NO: 27 | Rev-1 |
| CCAAATCCTTTCTCCCCAGTG | None | SEQ ID NO: 28 | Rev-2 |
| GTTTTCTGCTGTCTTTGGAACTTTG | None | SEQ ID NO: 29 | Rev-3 |

Cycling Reaction and Detection of Products. Oligonucleotide primers SEQ ID NO: 13 (For-1, 1× 5-nitroindole modification) and SEQ ID NO: 28 (Rev-2, unmodified) were 5'-end labeled using T4 polynucleotide kinase and γ-$^{32}$P-ATP as described above in section 4.3. Labeled primers were used in amplification reactions with the RatCP gene target as follows:

TABLE 7

Polynomial amplification using radiolabeled primers.

10 mM Tris pH 8.3
50 mM KCl
5.0 mM MgCl$_2$
1 mM dNTPs
1 × 10$^8$ copies Rat CP gene target DNA
200 nM unlabeled forward primer oligonucleotide
  (SEQ ID NOS: 13)
200 nM unlabeled reverse primer oligonucleotide
  (SEQ ID NOS: 28)
500,000 CPM $^{32}$P-labeled oligonucleotide
  (SEQ ID NO: 13 or 28)
2.5 units Amplitaq ™ Gold DNA polymerase (Applied Biosystems Inc., Foster City, CA)
25 µl final volume Reactions were conducted in a PTC-200 Peltier Thermal Cycler (MJ Research, Waltham, Mass.). Cycling conditions employed were: 95° C. for 15 minutes followed by 20, 30, or 45 cycles of a 3-step reaction with 95° C. for 15 seconds, 55° C. for 15 seconds, and 72° C. for 30 seconds, followed by incubation at 72° C. for 3 minutes. Reactions were stopped by mixing with an equal volume of 2× loading buffer; half of each reaction was loaded and run on a 15% polyacrylamide, 7M urea, 0.5× TBE gel (as described in Example 2). The gel was exposed to a Packard MP phosphor screen for 1 hour and visualized using a Packard Cyclone™ Storage Phosphor System (Packard Biosciences, Meriden, Conn.).

Results and Discussion

Adapting the nomenclature from FIGS. 2 and 3 to describe the specific amplification reaction of this example, 3 "top" strand species ("A", "C", and "E") and 3 "bottom" strand species ("B", "D", and "F") will be present. Species "A" is unlabeled input target top strand, species "C" is a "forward-primed" product of variable length made using input strand "B" as template, and species "E" is a "forward primed" product of 156 base length made from product species "D" as template (terminating at the 5'-base of the reverse primer). Species "B" is unlabeled input target bottom strand, species "D" is a "reverse-primed" product of variable length made using input strand "A" as template, and species "F" is a "reverse-primed" product of 137 base length made from both product species "C" and "E" as template. Product "F" terminates at the internal blocking group within the modified forward primer; if the blocking function of this group is "leaky", then species "F" will instead terminate at the 5'-base of the forward primer to result in a 156 base length product. Mathematically predicted yield of relevant species is:

TABLE 8

Predicted yield of reaction products in 2 primer polynomial amplification.

| Cycle # | Species "E" (For primer) | Species "F" (Rev primer) |
|---------|--------------------------|--------------------------|
| 20      | 190                      | 1330                     |
| 30      | 435                      | 4495                     |
| 45      | 990                      | 15180                    |

Figure 8:
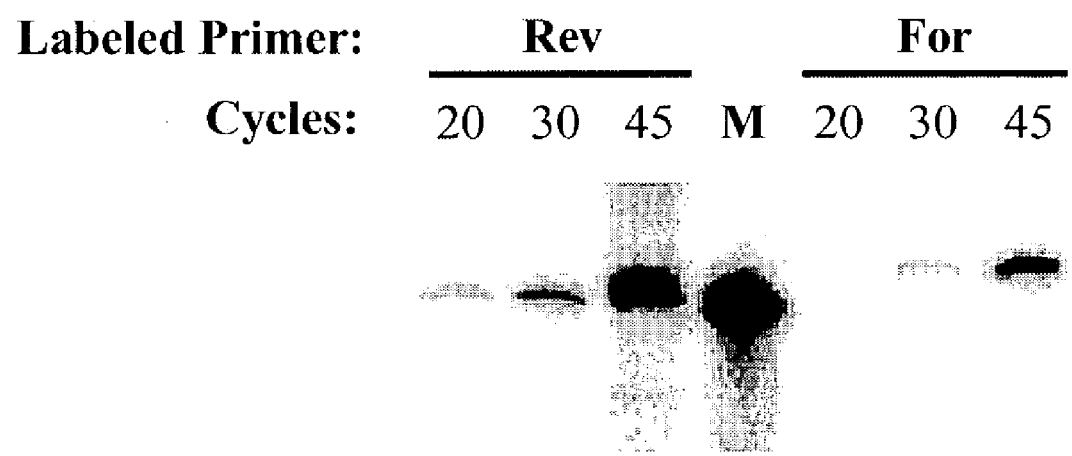
FIG. 8. Relative accumulation of products from a 2-primer polynomial amplification reaction. Polynomial amplification was conducted as described using both a 5'-$^{32}$P-labeled reverse (Rev) primer (SEQ ID NO: 28) and blocked forward (For) primer (SEQ ID NO: 13). The forward primer contains a single 5-nitroindole blocking group. Reactions were run for 20, 30, or 45 cycles as indicated. Reaction products were separated using PAGE and visualized using scintigraphy. A 130-base marker is included for reference in lane "M". Expected size of the forward reaction product is 156 bases. Expected size of the reverse reaction product is 137 bases.

From the relative intensity of amplification products visualized in FIG. 8, it is evident that amplification is occurring as band intensity increases with cycle number. It is further evident that reverse strand products (i.e., species "F") accumulate faster than forward strand products (i.e., species "E"). Reaction products at 20 and 30 cycles are a single species of the expected size. At 45 cycles, however, 2 products are visualized using the radiolabeled reverse primer, one with a size consistent with the expected 137 base product and a second that co-migrates with the longer forward product (156 bases). Presumably this longer band represents accumulation of reverse-primed species that escape termination by the blocking group in the modified forward primer.

In this example, a single 5-nitroindole base was incorporated in the forward primer (SEQ ID NO: 13). Results from Example 2, FIG. 5, demonstrate that a single insertion of 5-nitroindole offers incomplete blockade of DNA polymerase. As demonstrated in Example 3, FIG. 8, insertion of a single 5-nitroindole group does block DNA polymerase in the setting of cycling amplification and that this blockade is effective at lower cycle number (20–30 cycles). Blockade by a single 5-nitroindole group is incomplete (i.e., is "leaky") and full-length reaction products are readily detected at 45 cycles.

Example 4

Quantification of Amplification Products Using a Real-Time PCR Assay

The radiolabel assay of Example 3 demonstrates that reactions conducted using polynomial amplification amplify target DNA and that this amplification preferentially accumulates a specific single-stranded product as predicted. The radiolabel assay, however, is only semi-quantitative. A real-time PCR 5'-nuclease assay (U.S. Pat. No. 5,210,015) that is highly quantitative was used to better compare actual amplification yields with theoretical predictions.

Materials and Methods

Nucleic Acids. The Rat CP gene target and primers as described in Example 3, FIG. 7 and Table 6, was used for the amplification reactions of Example 4. A dual-labeled fluorescence-quenched probe (U.S. Pat. No. 5,538,848; Livak et al. *PCR Methods Appl.* 4:357–62.1995) was synthesized specific for the Rat CP gene target (SEQ ID NO: 30). Oligonucleotide primers For-3 (SEQ ID NO: 26) and Rev-3 (SEQ ID NO: 29) with probe oligonucleotide (SEQ ID NO: 30) constitute the real-time PCR assay and are positioned centrally within the Rat CP gene target such that amplification reactions conducted using primers For-1, For-2, Rev-1, and Rev-2 will produce products that can be quantitatively detected using the real-time PCR assay with primers For-3 and Rev-3.

Amplification reactions. Amplification reactions were performed as follows:

TABLE 9

Amplification Reaction Mix.

| | |
|---|---|
| 10 mM | Tris pH 8.3 |
| 50 mM | KCl |
| 5.0 mM | MgCl$_2$ |
| 200 nM | dNTPs |
| 1 × 10$^6$ copies | Rat CP gene target DNA |
| 200 nM (10 pmoles) | forward primer oligonucleotide |
| 200 nM (10 pmoles) | second (nested) forward primer oligonucleotide (optional) |
| 200 nM (10 pmoles) | reverse primer oligonucleotide |
| 2.5 units | Amplitaq ™ Gold DNA polymerase (Applied Biosystems Inc., Foster City, CA) |
| 50 µl | final volume |

Reactions were conducted in a PTC-200 Peltier Thermal Cycler (MJ Research, Waltham, Mass.). Cycling conditions employed were: 95° C. for 15 minutes followed by 10, 30, or 50 cycles of a 3-step reaction with 95° C. for 15 seconds, 55° C. for 15 seconds, and 72° C. for 30 seconds, followed by incubation at 72° C. for 3 minutes. Reactions were diluted to 100 µl volume with water after cycling. Three types of reactions were performed, including PCR amplification, 2-primer polynomial amplification, and 3-primer nested polynomial amplification. PCR reactions employed the unmodified For-1 primer (SEQ ID NO: 12) and the unmodified Rev-1 primer (SEQ ID NO: 27). The 2-primer polynomial amplifications used a modified For-1 primer (selected from the set including SEQ ID NOS: 13–18) and the unmodified Rev-1 primer (SEQ ID NO: 27). The 3-primer nested polynomial amplifications used a modified For-1 primer (selected from the set including SEQ ID NOS: 13–18), a modified For-2 primer (selected from the set including SEQ ID NOS: 19–25), and the unmodified Rev-1 primer (SEQ ID NO: 27).

Following amplification, reaction product yield was measured using the quantitative 5'-nuclease real-time PCR assay. A 1 µl aliquot of each amplification reaction (1% of the reaction) was used as target. PCR amplification was done using the Invitrogen Platinum Supermix-UDG (Carlsbad, Calif.) according to the manufacturer's directions. Reactions were 25 ul volume and comprised:

TABLE 10

PCR Reaction Mix for Real-time Assays.

| Component | Final Concentration |
|---|---|
| Tris pH 8.4 | 20 mM |
| KCl | 50 mM |
| MgCl$_2$ | 3.0 mM |
| dATP, dGTP, and dCTP, | 200 uM each |
| dUTP | 400 uM |
| Uracil-DNA-N-deglycosylase | 0.5 units |
| Taq DNA polymerase | 1.0 unit |
| Reference Dye | 50 nM |
| Primer For-3 (SEQ ID NO: 26) | 200 nM |
| Primer Rev-3 (SEQ ID NO: 29) | 200 nM |
| Probe (SEQ ID NO: 30) | 200 nM |
| Target DNA | 1 ul, from amplification reactions (or standards) |

Cycling conditions employed were: 50° C. for 2 minutes and 95° C. for 10 minutes followed by 40 cycles of 2-step PCR with 95° C. for 15 seconds and 60° C. for 1 minute. PCR and fluorescence measurements were done using an ABI Prism™ 7700 Sequence Detector (Applied Biosystems Inc., Foster City, Calif.). Control reactions were run with each experiment using known dilutions of the Rat CP gene target DNA (SEQ ID NO: 11) to establish a standard curve for quantitation including $1 \times 10^2$, $1 \times 10^4$, $1 \times 10^6$, and $1 \times 10^8$ target molecules. All data points were performed in triplicate. The test amplification reactions contained $1 \times 10^6$ molecules of input target DNA. A 1 ul aliquot (1/100, after dilution to 100 ul volume) was transferred to the real-time PCR assay, so baseline for the assay is $1 \times 10^4$ molecules of target. Any increase above $1 \times 10^4$ molecules represents amplification.

Figure 9:
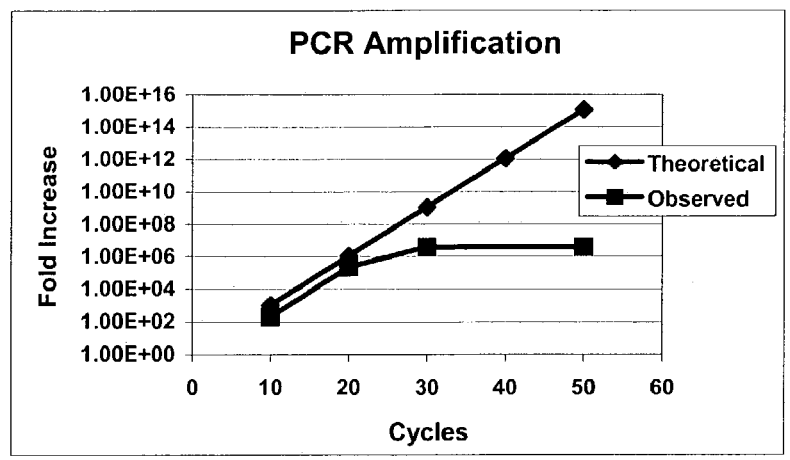
FIGS. 9A, 9B, and 9C. Theoretical versus observed yield for amplification reactions. Amplification reactions were performed and resulting products were quantitated using a real-time PCR 5'-nuclease assay using the target and probes of FIG. 7 and primers of Table 6. Reaction yield (fold increase from starting target number) is plotted on a logarithmic scale on the Y-axis against the cycle number on the X-axis. For polynomial amplification reactions, results obtained using primers with different blocking groups are also compared. A. Polymerase chain reaction. B. Two-Primer polynomial amplification. C. Three-Primer hemi-nested polynomial amplification.
Figure 9:
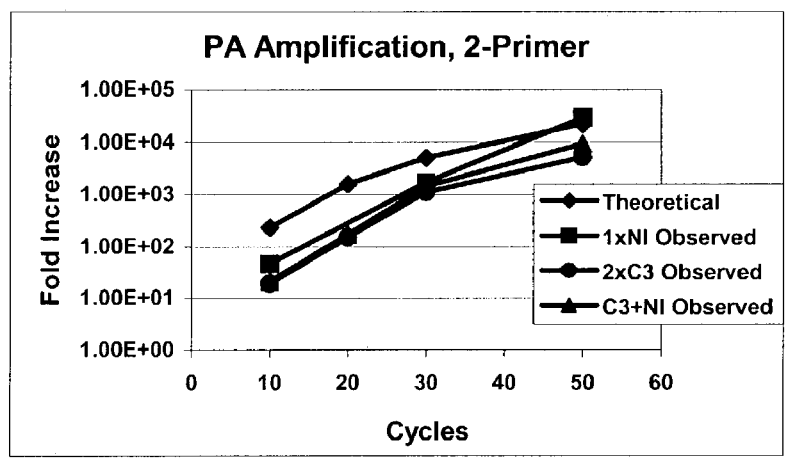
Figure 9:
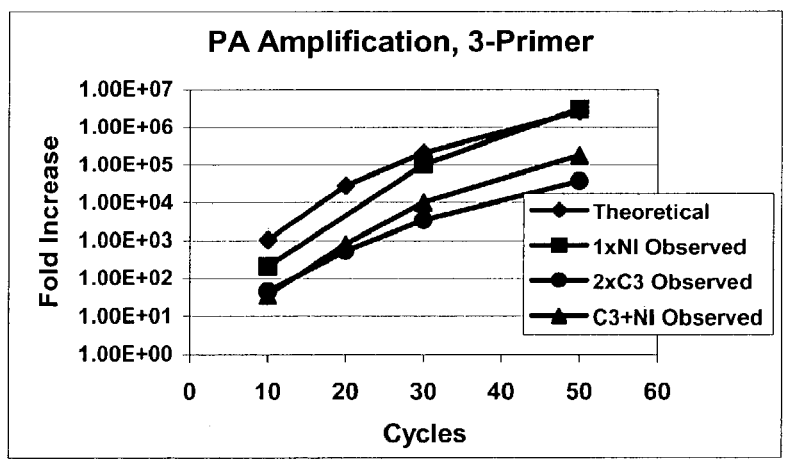

In a real-time PCR assay, the cycle threshold (Ct) value is defined as the cycle at which a statistically significant increase in fluorescence is detected above background. Lower Ct values indicate higher concentration of target DNA. Ct values were determined for standards and test amplification samples. Target copy number was determined for test samples by extrapolation against the standard curve. Amplification yield (fold increase) is measured relative to the input target ($1 \times 10^4$ molecules) and is shown in FIG. 9.

Results and Discussion

PCR amplification products initially accumulated in the expected amounts but reached plateau before 30 cycles. In the reaction outlined in Table 9, 10 pmoles of each primer ($6 \times 10^{12}$ molecules) were available as substrate and $1 \times 10^6$ copies of target template was input. Assuming 100% reaction efficiency, primers would be expected to be entirely consumed by cycle 23. As seen in FIG. 9A, PCR amplification did achieve plateau between cycles 10 and 30, consistent with this prediction.

Amplification results from 2-primer polynomial amplification are shown in FIG. 9B and results from 3-primer hemi-nested polynomial amplification are shown in FIG. 9C. Polynomial amplification products accumulated at about the expected amounts and did not plateau within the cycle range tested.

Performance of different forward primers having various blocking groups (Table 6) was compared and is included in FIGS. 9B and 9C. Polynomial amplification using primers having a single 5-nitroindole block (SEQ ID NOS: 13 and 20) achieve slightly higher yield than predicted; in practice, yields are generally expected to be below theoretical predictions as reactions do not proceed with 100% efficiency. In this case, it is likely that the single blocking group employed is "leaky" and that yields exceed expectation on this basis. Yields achieved using double-blocked forward primers (SEQ ID NOS: 16 and 23 or 17 and 24) were below theoretical levels and fit better with expectation. In summary, Example 4 demonstrates that amplification occur using the method of the invention and further demonstrate that product accumulation follows the mathematically predicted course. Of the various block groups and combinations thereof tested, use of a C3-Spacer with a 5-nitroindole in tandem provided the best overall performance, resulting in good overall yield with no evidence for "leakage".

Example 5

Low Contamination Risk for Products of Polynomial Amplification Reaction

Amplification using the polynomial method employs blocked primers in only one orientation; the primer in the opposite direction is replication competent. During polynomial amplification, reaction products made with the unmodified primer and using the parent target nucleic acid as template will be "amplification competent" and contribute to carry-over contamination. However, this species undergoes simple linear amplification and will only accumulate at the rate of 1 copy per cycle. Most product strands made using the polynomial amplification method are replication incompetent such that DNA synthesis products that use this product as template will terminate and will not provide a priming site for additional cycles of amplification. Polynomial amplification products will have little capacity to support carry-over contamination (i.e., they will not support re-amplification). Evidence for reduced contamination capacity for polynomial amplification products was assessed using a real-time PCR assay and the Rat CP gene target system.

Materials and Methods

Nucleic Acids. Primers, probe, and target nucleic acids are described in Table 3, Table 3, and FIG. 7. Primers employed include blocked versions of For-1 and For-2 with unmodified Rev-1. In Example 4, polynomial amplification products were quantitatively assayed using a real-time PCR assay wherein the assay amplicon (comprising primer For-3, SEQ ID NO: 26, primer Rev-3, SEQ ID NO: 29, and probe, SEQ ID NO: 30) was positioned internally within the priming sites employed in polynomial amplification. In addition to this assay, the polynomial reaction products were assayed using unmodified For-1 (SEQ ID NO: 12) and unmodified Rev-3 primers (SEQ ID NO: 29) with the same probe (SEQ ID NO: 30); this configuration will test for the ability of polynomial reaction products to support additional rounds of amplification (i.e., carry-over contamination or re-amplification).

Amplification reactions and real-time PCR assays. PCR reactions were done using the method outlined in Example 4, Table 9 using primers For-1 (SEQ ID NO: 12) and Rev-1 (SEQ ID NO: 27). Polynomial amplification reactions were done using the method outlined in Example 4, Table 9 using forward primers having different modifications or combinations of different modifications (Table 6) to compare if different blocking groups are more or less effective in reducing the capacity of reaction products for carry-over contamination.

Real-time PCR assays were performed as outlined in Example 4, Table 9 to determine amplification reaction yields. To measure the capacity of reaction products to support carry-over re-amplification, the assay was modified such that forward primer For-1 (SEQ ID NO: 12) was used in place of For-3 (SEQ ID NO: 26). Cycle threshold values were determined and quantitative yields were calculated by extrapolation from a standard curve.

Results and Discussion

Figure 10:
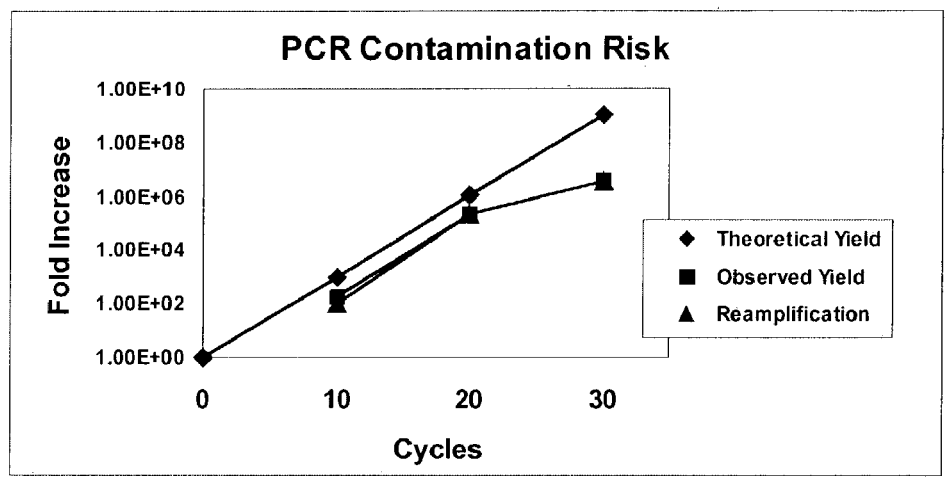
FIGS. 10A, 10B, and 10C. Carry-over contamination risk for PCR vs. polynomial amplification reaction products. Amplification reactions were performed and resulting products were quantitated using a real-time PCR 5'-nuclease assay. Yield was determined using an assay wherein the primers were positioned internal to the original amplification primers. Contamination capacity was determined using an assay wherein the primers were positioned at the same site used in the original amplification reaction ("reamplification"). A. Polymerase chain reaction. B. Two-Primer polynomial amplification. C. Three-Primer hemi-nested polynomial amplification.
Figure 10:
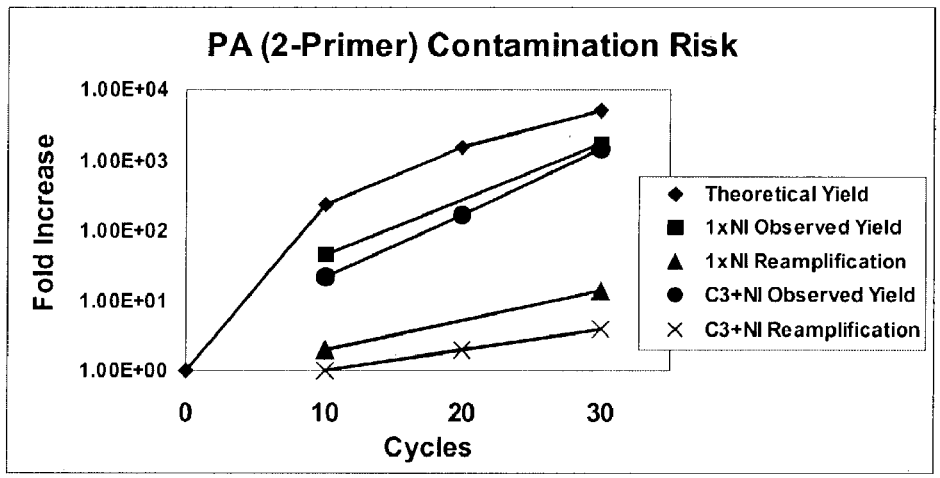
Figure 10:
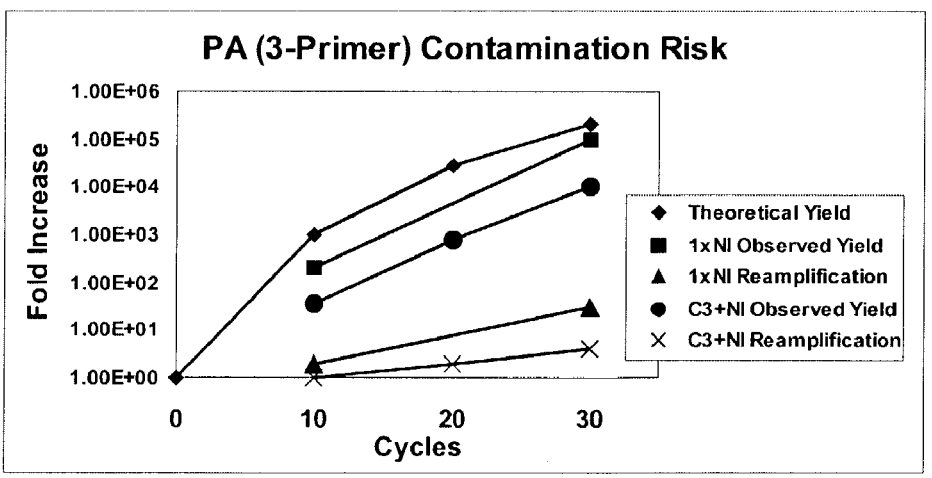

For PCR reactions, reaction yield and capacity to support carry-over contamination are identical (FIG. 10A). For polynomial amplification reactions, reaction yield is substantially higher than the capacity of the reaction products to support added amplification. The use of double-blocked primers (FIG. 10C) SEQ ID NOS: 17 and 24, having a C3-Spacer and a 5-nitroindole insertion in tandem, was more effective in reducing carry-over capacity of reaction products than was use of single-blocked primers (FIG. 10B) SEQ ID NOS: 13 and 20, having one 5-nitroindole insertion. Although a 30-fold contamination risk would be predicted for polynomial amplification, only a 10-fold increase was observed (see reamplification curves in FIGS. 10B and 10C). A factor likely contributing to the lower contamination seen is that amplification proceeds at less than 100% efficiency. In summary, Example 5 demonstrates the utility of the present invention to reduce risk for carry-over contamination from amplification reaction products through the use of blocked primers in only a single orientation in an amplification reaction.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed is:

1. A method for amplifying a nucleotide sequence of interest from a nucleic acid, which method comprises:
   (a) contacting the nucleic acid with a primer set, which primer set comprises (i) a first non-replicable primer that hybridizes to the nucleic acid and (ii) a replicable primer that hybridizes to a primer extension product generated by replication of the nucleic acid from the first non-replicable primer; under conditions such that a first generation primer extension product that is capable of hybridizing to the replicable primer is produced using the nucleic acid as a template and the first non-replicable primer as the primer;
   (b) separating the first generation primer extension products from their respective templates to produce single-stranded molecules;
   (c) treating the first generation primer extension products and the nucleic acid with the primers of step (a) under conditions such that second generation primer extension products are produced using the first generation primer extension products as templates for the replicable primer, and the nucleic acid as a template for the first non-replicable primer; and
   (d) repeating steps (b) and (c) as many times as desired to amplify the nucleotide sequence;
   wherein the primer extension products contain at least a portion of the sequence of the nucleotide sequence of interest or its complement;
   wherein the primer set further comprises a second non-replicable primer which hybridizes to the nucleic acid and to the second generation extension product; and
   wherein the second non-replicable primer has a lower concentration than the first non-replicable primer.

2. The method of claim 1 wherein the second non-replicable primer is reversibly unable to initiate primer extension.

3. The method of claim 2 wherein the second non-replicable primer possesses a photolabile-blocking group which renders the second non-replicable primer unable to initiate primer extension.

4. The method of claim 1 wherein the second non-replicable primer has a lower melting temperature than the first non-replicable primer.

5. The method according to claim 1, wherein the primer set further comprises a non-replicable primer which hybridizes to the (i) nucleic acid, (ii) to the second generation extension product; and (iii) to a primer extension product generated by replication from the replicable primer and extension products of the second non-replicable primer.

* * * * *

SEQUENCE LISTING

<160> NUMBER OF SEQ ID NOS: 34

<210> SEQ ID NO 1
<211> LENGTH: 18
<212> TYPE: DNA
<213> ORGANISM: Artificial Sequence
<220> FEATURE:
<223> OTHER INFORMATION: PCR primer

<400> SEQUENCE: 1
gtgaccggca gcaaaatg                                              18

<210> SEQ ID NO 2
<211> LENGTH: 45
<212> TYPE: DNA
<213> ORGANISM: Artificial Sequence
<220> FEATURE:

```
<223> OTHER INFORMATION: oligonucleotide control

<400> SEQUENCE: 2
actttagcga tagtcttttg cgttatgcat tttgctgccg gtcac          45

<210> SEQ ID NO 3
<211> LENGTH: 45
<212> TYPE: DNA
<213> ORGANISM: Artificial Sequence
<220> FEATURE:
<223> OTHER INFORMATION: oligonucleotide
<220> FEATURE:
<221> NAME/KEY: modified_base
<222> LOCATION: (19)..(19)
<223> OTHER INFORMATION: where u is 2'-O-methyl uracil

<400> SEQUENCE: 3
actttagcga tagtctttug cgttatgcat tttgctgccg gtcac          45

<210> SEQ ID NO 4
<211> LENGTH: 45
<212> TYPE: DNA
<213> ORGANISM: Artificial Sequence
<220> FEATURE:
<223> OTHER INFORMATION: oligonucleotide
<220> FEATURE:
<221> NAME/KEY: modified_base
<222> LOCATION: (18)..(19)
<223> OTHER INFORMATION: where u is 2'-O-methyl uracil

<400> SEQUENCE: 4
actttagcga tagtcttuug cgttatgcat tttgctgccg gtcac          45

<210> SEQ ID NO 5
<211> LENGTH: 45
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (19)..(19)
<223> OTHER INFORMATION: where n is 5-nitroindole

<400> SEQUENCE: 5
actttagcga tagtctttng cgttatgcat tttgctgccg gtcac          45

<210> SEQ ID NO 6
<211> LENGTH: 45
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (18)..(19)
<223> OTHER INFORMATION: where n is 5-nitroindole

<400> SEQUENCE: 6
actttagcga tagtcttnng cgttatgcat tttgctgccg gtcac          45

<210> SEQ ID NO 7
<211> LENGTH: 44
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
```

```
<222> LOCATION: (18)..(19)
<223> OTHER INFORMATION: between residues 18 and 19 is a d-spacer

<400> SEQUENCE: 7
actttagcga tagtctttgc gttatgcatt ttgctgccgg tcac            44

<210> SEQ ID NO 8
<211> LENGTH: 42
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (17)..(18)
<223> OTHER INFORMATION: between residues 17 and 18 are two d-spacers

<400> SEQUENCE: 8
actttagcga tagtcttcgt tatgcattttt gctgccggtc ac              42

<210> SEQ ID NO 9
<211> LENGTH: 44
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (18)..(19)
<223> OTHER INFORMATION: between residues 18 and 19 is a C3-Spacer

<400> SEQUENCE: 9
actttagcga tagtctttgc gttatgcatt ttgctgccgg tcac            44

<210> SEQ ID NO 10
<211> LENGTH: 43
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (17)..(18)
<223> OTHER INFORMATION: between residues 17 and 18 are two C3-Spacers

<400> SEQUENCE: 10
actttagcga tagtcttgcg ttatgcatttt tgctgccggt cac             43

<210> SEQ ID NO 11
<211> LENGTH: 195
<212> TYPE: DNA
<213> ORGANISM: Rattus norvegicus

<400> SEQUENCE: 11
taatacgact cactatagac atggtcaacc ccaccgtgtt cttcgacatc acggctgatg     60
gcgagccctt gggtcgcgtc tgcttcgagc tgtttgcaga caaagttcca agacagcag    120 aaaactttcg tgctctgagc actggggaga aaggatttgg ctataagatg atacactccg    180
acataacgtg gatcc                                                     195

<210> SEQ ID NO 12
<211> LENGTH: 25
<212> TYPE: DNA
<213> ORGANISM: Artificial Sequence
<220> FEATURE:
<223> OTHER INFORMATION: oligonucleotide primer
```

```
<400> SEQUENCE: 12
acgactcact atagacatgg tcaac                                              25

<210> SEQ ID NO 13
<211> LENGTH: 25
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<222> LOCATION: (19)..(19)
<223> OTHER INFORMATION: where n is 5-nitroindole

<400> SEQUENCE: 13
acgactcact atagacatng tcaac                                              25

<210> SEQ ID NO 14
<211> LENGTH: 25
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<222> LOCATION: (18)..(19)
<223> OTHER INFORMATION: where n is 5-nitroindole

<400> SEQUENCE: 14
acgactcact atagacanng tcaac                                              25

<210> SEQ ID NO 15
<211> LENGTH: 24
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<222> LOCATION: (18)..(19)
<223> OTHER INFORMATION: between residues 18 and 19 is a C3-Spacer

<400> SEQUENCE: 15
acgactcact atagacatgt caac                                               24

<210> SEQ ID NO 16
<211> LENGTH: 23
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<222> LOCATION: (17)..(18)
<223> OTHER INFORMATION: between residues 17 and 18 are two C3-Spacers

<400> SEQUENCE: 16
acgactcact atagacagtc aac                                                23

<210> SEQ ID NO 17
<211> LENGTH: 24
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<222> LOCATION: (18)..(18)
<223> OTHER INFORMATION: where n is 5-nitroindole
```

```
<220> FEATURE:
<221> NAME/KEY: misc_feature
<222> LOCATION: (18)..(19)
<223> OTHER INFORMATION: between residues 18 and 19 is a C3-Spacer

<400> SEQUENCE: 17
acgactcact atagacangt caac                                              24

<210> SEQ ID NO 18
<211> LENGTH: 24
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<222> LOCATION: (17)..(18)
<223> OTHER INFORMATION: where n is 5-nitroindole
<220> FEATURE:
<221> NAME/KEY: misc_feature
<222> LOCATION: (18)..(19)
<223> OTHER INFORMATION: between residues 18 and 19 is a C3-Spacer

<400> SEQUENCE: 18
acgactcact atagacnngt caac                                              24

<210> SEQ ID NO 19
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 19
ccaccgtgtt cttcgacatc                                                   20

<210> SEQ ID NO 20
<211> LENGTH: 20
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<222> LOCATION: (14)..(14)
<223> OTHER INFORMATION: where n is 5-nitroindole

<400> SEQUENCE: 20
ccaccgtgtt cttngacatc                                                   20

<210> SEQ ID NO 21
<211> LENGTH: 20
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<222> LOCATION: (13)..(14)
<223> OTHER INFORMATION: where n is 5-nitroindole

<400> SEQUENCE: 21
ccaccgtgtt ctnngacatc                                                   20

<210> SEQ ID NO 22
<211> LENGTH: 19
<212> TYPE: DNA
<213> ORGANISM: Artificial Sequence
<220> FEATURE:
```

```
<223> OTHER INFORMATION: oligonucleotide primer
<220> FEATURE:
<221> NAME/KEY: misc_feature
<222> LOCATION: (13)..(14)
<223> OTHER INFORMATION: between residues 13 and 14 is a C3-Spacer

<400> SEQUENCE: 22
ccaccgtgtt cttgacatc                                                19

<210> SEQ ID NO 23
<211> LENGTH: 18
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<222> LOCATION: (12)..(13)
<223> OTHER INFORMATION: between residues 12 and 13 are two C3-Spacers

<400> SEQUENCE: 23
ccaccgtgtt ctgacatc                                                 18

<210> SEQ ID NO 24
<211> LENGTH: 19
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<222> LOCATION: (13)..(13)
<223> OTHER INFORMATION: where n is 5-nitroindole
<220> FEATURE:
<221> NAME/KEY: misc_feature
<222> LOCATION: (13)..(14)
<223> OTHER INFORMATION: between residues 13 and 14 is a C3-Spacer

<400> SEQUENCE: 24
ccaccgtgtt ctngacatc                                                19

<210> SEQ ID NO 25
<211> LENGTH: 19
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<222> LOCATION: (12)..(13)
<223> OTHER INFORMATION: where n is 5-nitroindole
<220> FEATURE:
<221> NAME/KEY: misc_feature
<222> LOCATION: (13)..(14)
<223> OTHER INFORMATION: between residues 13 and 14 is a C3-Spacer

<400> SEQUENCE: 25
ccaccgtgtt cnngacatc                                                19

<210> SEQ ID NO 26
<211> LENGTH: 16
<212> TYPE: DNA
<213> ORGANISM: Artificial Sequence
<220> FEATURE:
<223> OTHER INFORMATION: oligonucleotide primer

<400> SEQUENCE: 26
atggcgagcc cttggg                                                   16
```

```
<210> SEQ ID NO 27
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 27
gatccacgtt atgtcggagt g                                         21

<210> SEQ ID NO 28
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 28
ccaaatcctt tctccccagt g                                         21

<210> SEQ ID NO 29
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 29
gttttctgct gtctttggaa ctttg                                     25

<210> SEQ ID NO 30
<211> LENGTH: 23
<212> TYPE: DNA
<213> ORGANISM: Artificial Sequence
<220> FEATURE:
<223> OTHER INFORMATION: probe oligonucleotide

<400> SEQUENCE: 30
cgcgtctgct tcgagctgtt tgc                                       23

<210> SEQ ID NO 31
<211> LENGTH: 45
<212> TYPE: DNA
<213> ORGANISM: Artificial Sequence
<220> FEATURE:
<223> OTHER INFORMATION: oligonucleotide
<220> FEATURE:
<221> NAME/KEY: modified_base
<222> LOCATION: (16)..(19)
<223> OTHER INFORMATION: where u is 2'-O-methyl uracil

<400> SEQUENCE: 31
actttagcga tagtcuuuug cgttatgcat tttgctgccg gtcac               45

<210> SEQ ID NO 32
<211> LENGTH: 45
<212> TYPE: DNA
<213> ORGANISM: Artificial Sequence
<220> FEATURE:
<223> OTHER INFORMATION: oligonucleotide
<220> FEATURE:
<221> NAME/KEY: modified_base
<222> LOCATION: (14)..(14)
<223> OTHER INFORMATION: where u is 2'-O-methyl uracil
<220> FEATURE:
<221> NAME/KEY: modified_base
<222> LOCATION: (15)..(15)
<223> OTHER INFORMATION: where c is 2'-O-methyl cytosine
<220> FEATURE:
```

```
<221> NAME/KEY: modified_base
<222> LOCATION: (16)..(19)
<223> OTHER INFORMATION: where u is 2'-O-methyl uracil

<400> SEQUENCE: 32
actttagcga tagucuuuug cgttatgcat tttgctgccg gtcac           45

<210> SEQ ID NO 33
<211> LENGTH: 44
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (18)..(18)
<223> OTHER INFORMATION: where n is 5-nitroindole
<220> FEATURE:
<221> NAME/KEY: misc_feature
<222> LOCATION: (18)..(19)
<223> OTHER INFORMATION: between residues 18 and 19 is a C3-Spacer

<400> SEQUENCE: 33
actttagcga tagtcttngc gttatgcatt ttgctgccgg tcac            44

<210> SEQ ID NO 34
<211> LENGTH: 44
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (17)..(18)
<223> OTHER INFORMATION: where n is 5-nitroindole
<220> FEATURE:
<221> NAME/KEY: misc_feature
<222> LOCATION: (18)..(19)
<223> OTHER INFORMATION: between residues 18 and 19 is a C3-Spacer

<400> SEQUENCE: 34
actttagcga tagtctnngc gttatgcatt ttgctgccgg tcac            44
```